US010155702B2

(12) United States Patent
Iaccino et al.

(10) Patent No.: US 10,155,702 B2
(45) Date of Patent: *Dec. 18, 2018

(54) PROCESSES AND SYSTEMS FOR CONVERTING HYDROCARBONS TO CYCLOPENTADIENE

(71) Applicant: ExxonMobil Chemical Patents Inc., Baytown, TX (US)

(72) Inventors: Larry L. Iaccino, Seabrook, TX (US); Romain O. V. Lemoine, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 82 days.

This patent is subject to a terminal disclaimer.

(21) Appl. No.: 15/288,430

(22) Filed: Oct. 7, 2016

(65) Prior Publication Data

US 2017/0121251 A1    May 4, 2017

Related U.S. Application Data

(60) Provisional application No. 62/250,677, filed on Nov. 4, 2015.

(51) Int. Cl.
C07C 5/327 (2006.01)
C07C 5/32 (2006.01)
(Continued)

(52) U.S. Cl.
CPC .............. C07C 5/373 (2013.01); B01J 29/44 (2013.01); B01J 29/63 (2013.01); B01J 29/90 (2013.01);
(Continued)

(58) Field of Classification Search
CPC ............ C07C 5/327; C07C 5/32; C07C 5/333
(Continued)

(56) References Cited

U.S. PATENT DOCUMENTS 2,344,330 A    3/1944  Sturgeon
2,438,398 A    3/1948  Kennedy et al.
(Continued)

FOREIGN PATENT DOCUMENTS

DE    2535809    3/1976
EP    2586524    5/2013
(Continued)

OTHER PUBLICATIONS

U.S. Appl. No. 15/288,412, filed Oct. 7, 2016, Iaccino et al.
(Continued)

Primary Examiner — Thuan D Dang

(57) ABSTRACT

This invention relates to a process for converting acyclic $C_5$ hydrocarbons to cyclopentadiene in a reactor system, wherein the process comprises a reaction interval comprising: cyclically providing to the reactor system a feedstock comprising acyclic $C_5$ hydrocarbons; contacting the feedstock and with a particulate material comprising a catalyst material in a first reaction zone under reaction conditions to convert at least a portion of the acyclic $C_5$ hydrocarbons to a first effluent comprising cyclopentadiene; and a reheating interval comprising: cyclically halting the feedstock to the first reaction zone; and providing a reheating gas to the first reaction zone to reheat the particulate material.

24 Claims, 6 Drawing Sheets

| Reactor(n)   | Reaction  | Reheating |           |
|--------------|-----------|-----------|-----------|
| Reactor(n+1) | Reheating | Reaction  | Reheating |
| Reactor(n+2) | Reaction  | Reheating | Reaction  |
| Reactor(n+3) | Reheating | Reaction  |           |
| Time         |           |           |           |
| 0            |           | Xmin      | 2Xmin     |

| Reactor(n+4) | Regeneration | ~YDays |

(51) Int. Cl.

| | |
|---|---|
| C07C 5/333 | (2006.01) |
| C07C 5/373 | (2006.01) |
| B01J 29/44 | (2006.01) |
| B01J 29/63 | (2006.01) |
| B01J 29/90 | (2006.01) |

(52) U.S. Cl.
CPC ...... *C07C 2101/10* (2013.01); *C07C 2529/44* (2013.01); *C07C 2601/10* (2017.05); *Y02P 20/584* (2015.11); *Y02P 20/588* (2015.11)

(58) Field of Classification Search
USPC .................................... 585/365, 366, 369
See application file for complete search history.

(56) References Cited

U.S. PATENT DOCUMENTS

| | | | |
|---|---|---|---|
| 2,438,399 | A | 3/1948 | Kennedy et al. |
| 2,438,400 | A | 3/1948 | Hetzel et al. |
| 2,438,401 | A | 3/1948 | Kennedy et al. |
| 2,438,402 | A | 3/1948 | Kennedy et al. |
| 2,438,403 | A | 3/1948 | Kennedy et al. |
| 2,438,404 | A | 3/1948 | Hetzel et al. |
| 2,982,798 | A | 5/1961 | Hachmuth et al. |
| 3,862,252 | A | 1/1975 | Matsumura et al. |
| 3,953,368 | A | 4/1976 | Sinfelt |
| 4,581,339 | A | 4/1986 | Bhatt et al. |
| 4,886,926 | A | 12/1989 | Dessau et al. |
| 4,996,387 | A | 2/1991 | Gerhold et al. |
| 5,192,728 | A | 3/1993 | Dessau et al. |
| 5,254,787 | A | 10/1993 | Dessau |
| 5,284,986 | A | 2/1994 | Dessau |
| 5,315,056 | A | 5/1994 | Feldman et al. |
| 5,406,011 | A | 4/1995 | Radcliffe et al. |
| 5,510,557 | A | 4/1996 | Gartside et al. |
| 5,633,421 | A | 5/1997 | Iezzi et al. |
| 6,392,113 | B1 | 5/2002 | Gartside |
| 7,622,623 | B2 | 11/2009 | Fridman et al. |
| 7,973,207 | B2 | 7/2011 | Fridman et al. |
| 8,188,328 | B2 | 5/2012 | Fridman et al. |
| 2017/0121249 | A1 | 5/2017 | Iaccino et al. |
| 2017/0121250 | A1 | 5/2017 | Iaccino et al. |
| 2017/0121252 | A1 | 5/2017 | Iaccino et al. |
| 2017/0121255 | A1 | 5/2017 | Iaccino etal. |

FOREIGN PATENT DOCUMENTS

| | | |
|---|---|---|
| WO | WO 89/04818 | 6/1989 |
| WO | WO95/23123 | 8/1995 |

OTHER PUBLICATIONS

U.S. Appl. No. 62/250,674, filed Nov. 4, 2015, Iaccino et al.
U.S. Appl. No. 62/250,680, filed Nov. 4, 2015, Iaccino et al.
U.S. Appl. No. 62/250,693, filed Nov. 4, 2015, Iaccino et al.
U.S. Appl. No. 62/250,677, filed Nov. 4, 2015, Iaccino et al.
U.S. Appl. No. 62/250,682, filed Nov. 4, 2015, Iaccino et al.
U.S. Appl. No. 62/250,697, filed Nov. 4, 2015, Iaccino.
Bricker, J.C. et al., "*Advanced Catalytic Dehydrogenation Technologies for Production of Olefins*," Topics in Catalysis, 2012, vol. 55, pp. 1309-1314.
Ercan, et al., "*Reactor Performance and Stability in an Alternating Reaction-Reheat Paraffin Dehydrogenation System*," The Canadian Journal of Chemical Engineering, 1996, vol. 74, 626-637.
Fel'dblyum, V.S., et al. "*Cyclization and Dehydrocyclization of $C_5$ Hydrocarbons over Platinum Nanocatalysts and in the Presence of Hydrogen Sulfide*," Doklady Chemistry, 2009, vol. 424, Part 2, pp. 27-30.
Kanazirev, V., et al. "*Conversion of $C_8$ Aromatics and n-Pentane Over $Ga_2O_3$/HZSM-5 Mechanically Mixed Catalysts*", Catalysis Letters, 1991, vol. 9, pp. 35-42.
Kennedy, R.M. et al., "*Formation of Cyclopentadiene from 1,3-Pentadiene*," Industrial and Engineering Chemistry, 1950, vol. 42, No. 3, pp. 547-552.
Li, X., et al. "*Catalytic Dehydroisomerization of n-alkanes to Isoalkenes*," Journal of Catalysis, 2008, vol. 255, pp. 134-137.
Lopez, C.M., et al. "*n-Pentane Hydroisomerization on Pt Containing HZSM-5, HBEA and SAPO-11*," Catalysis Letters, 2008, vol. 122, pp. 267-273.
Marcinkowski, T.E., "*Isomerization and Dehydrocyclization of 1,3-Pentadiene*," Retrospective Theses and Dissertations, 1979, Paper 433, pp. 1-110.
Nawaz, Z., "*Light Alkane Dehydrogenation to Light Olefin Technologies: A Comprehensive Review*," Rev. Chem. Eng., 2015, vol. 31 (5), pp. 413-436.
Sattler, et al. "*Catalytic Dehydrogenation of Light Alkanes on Metals and Metal Oxides*", Chemical Reviews, vol. 114, No. 20, Oct. 22, 2014, pp. 10613-10653.
Seo, et al., "*Repetitive Control of CATOFIN Process*," Korean J. Chem. Eng., 2007, vol. 24(6), pp. 921-926.
Vora, B.V., "*Development of Dehydrogenation Catalysts and Processes*," Topics in Catalysis, 2012, vol. 55, pp. 1297-1308.
Xu, Y., "*Methane activation without using oxidants over Mo/HZSM-5 zeolite catalysts*," Catalysis Letters, 1995, vol. 30, pp. 135-149.

PROCESSES AND SYSTEMS FOR CONVERTING HYDROCARBONS TO CYCLOPENTADIENE

CROSS REFERENCE TO RELATED APPLICATIONS

This invention claims priority to and the benefit of U.S. Ser. No. 62/250,677, filed Nov. 4, 2015. This application relates to U.S. Ser. No. 62/250,680, filed Nov. 4, 2015, U.S. Ser. No. 62/250,682, filed Nov. 4, 2015, and U.S. Ser. No. 62/250,697, filed Nov. 4, 2015.

FIELD OF THE INVENTION

This invention relates to reactors useful for processes for the conversion of acyclic $C_5$ feedstock to a product comprising cyclic $C_5$ compounds.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. Cyclopentadiene is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced if additional CPD could be produced at unconstrained rates and preferably at a cost lower than recovery from steam cracking. Co-production of other cyclic $C_5$'s is also desirable. Cyclopentane and cyclopentene can have high value as solvents, while cyclopentene may be used as a comonomer to produce polymers and as a starting material for other high value chemicals.

It would be advantageous to be able to produce cyclic $C_5$ compounds including CPD as the primary product from plentiful $C_5$ feedstock using a catalyst system to produce CPD, while minimizing production of light ($C_{4-}$) byproducts. While lower hydrogen content (for example, cyclics, alkenes, and dialkenes) could be preferred because the reaction endotherm is reduced and thermodynamic constraints on conversion are improved, non-saturates are more expensive than saturate feedstock. Linear $C_5$ skeletal structure is preferred over branched $C_5$ skeletal structures due to both reaction chemistry and the lower value of linear $C_5$ relative to branched $C_5$ (due to octane differences). An abundance of $C_5$ is available from unconventional gas and shale oil, as well as reduced use in motor fuels due to stringent environmental regulations. $C_5$ feedstock may also be derived from bio-feeds.

Various catalytic dehydrogenation technologies are currently used to produce mono-and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization, which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics, such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_{5S}$ to cyclic $C_{5S}$. These Pt supported on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 hr$^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_2$-$C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct.

U.S. Pat. Nos. 2,438,398; 2,438,399; 2,438,400; 2,438,401; 2,438,402; 2,438,403; and U.S. Pat. No. 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al., in "Cyclization and dehydrocyclization of $C_5$ hydrocarbons over platinum nanocatalysts and in the presence of hydrogen sulfide," Doklady Chemistry, vol. 424, pp. 27-30, 2009, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt$—$Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

López et al., in "n-Pentane Hydroisomerization on Pt Containing HZSM-5, HBEA and SAPO-11," Catalysis Letters, vol. 122, pp. 267-273, 2008, studied reactions of n-pentane on Pt-containing zeolites, including H-ZSM-5. At intermediate temperatures (250-400° C.), they reported efficient hydroisomerization of n-pentane on the Pt-zeolites with no discussion of cyclopentene formation. It is desirable to avoid this deleterious chemistry as branched $C_5$ do not produce cyclic $C_5$ as efficiently as linear $C_5$, as discussed above.

Li et al., in "Catalytic dehydroisomerization of n-alkanes to isoalkenes," Journal of Catalysis, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

U.S. Pat. No. 5,633,421 discloses a process for dehydrogenating $C_2$-$C_5$ paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421 nor U.S. Pat. No. 2,982,798 disclose production of CPD from acyclic $C_5$ hydrocarbons, which are desirable as feedstock because they are plentiful and low cost.

Further, many challenges exist in designing an on-purpose CPD production process. For example, the reaction converting $C_5$ hydrocarbons to CPD is extremely endothermic and is favored by low pressure and high temperature, but significant cracking of n-pentane and other $C_5$ hydrocarbons can occur at a relatively low temperature (e.g., 450° C.-500° C.). Further challenges include loss of catalyst activity due to coking during the process and further processing needed to remove coke from the catalyst, and the inability to use oxygen-containing gas to directly provide heat input to the reactor without damaging the catalyst.

Hence, there remains a need for a process to convert acyclic $C_5$ feedstock to non-aromatic, cyclic $C_5$ hydrocarbon, namely cyclopentadiene, preferably at commercial rates and conditions. Further, there is a need for a catalytic process targeted for the production of cyclopentadiene, which generates cyclopentadiene in high yield from plentiful $C_5$ feedstocks without excessive production of $C_{4-}$ cracked products and with acceptable catalyst aging properties. Additionally, there is a need for processes and systems for on-purpose CPD production from acyclic $C_5$ hydrocarbons, which address the above-described challenges.

SUMMARY OF THE INVENTION

In one aspect, this invention relates to a process for converting acyclic $C_5$ hydrocarbons to cyclopentadiene in a reactor system, wherein the process comprises a reaction interval comprising: cyclically providing to the reactor system a feedstock comprising acyclic $C_5$ hydrocarbons; contacting the feedstock with a particulate material comprising a catalyst material in a first reaction zone under reaction conditions to convert at least a portion of the acyclic $C_5$ hydrocarbons to a first effluent comprising cyclopentadiene, and a reheating interval comprising: cyclically halting the feedstock to the first reaction zone; and providing a reheating gas to the first reaction zone to reheat the particulate material.

In another aspect, this invention also relates to a reaction system for converting acyclic $C_5$ hydrocarbons to cyclopentadiene, wherein the reaction system comprises: a feedstock stream comprising acyclic $C_5$ hydrocarbons; a first effluent stream comprising cyclopentadiene; a reheating gas stream and at least one reactor operated under reaction conditions to convert at least a portion of the acyclic $C_5$ hydrocarbons to cyclopentadiene; wherein the at least one reactor comprises: a particulate material comprising a catalyst material; a feedstock inlet for providing the feedstock stream and/or the reheating gas stream to the reaction system; and an effluent outlet for removal of the first effluent stream and/or the reheating gas stream.

DETAILED DESCRIPTION OF THE INVENTION

I. Definitions

Figure 1:
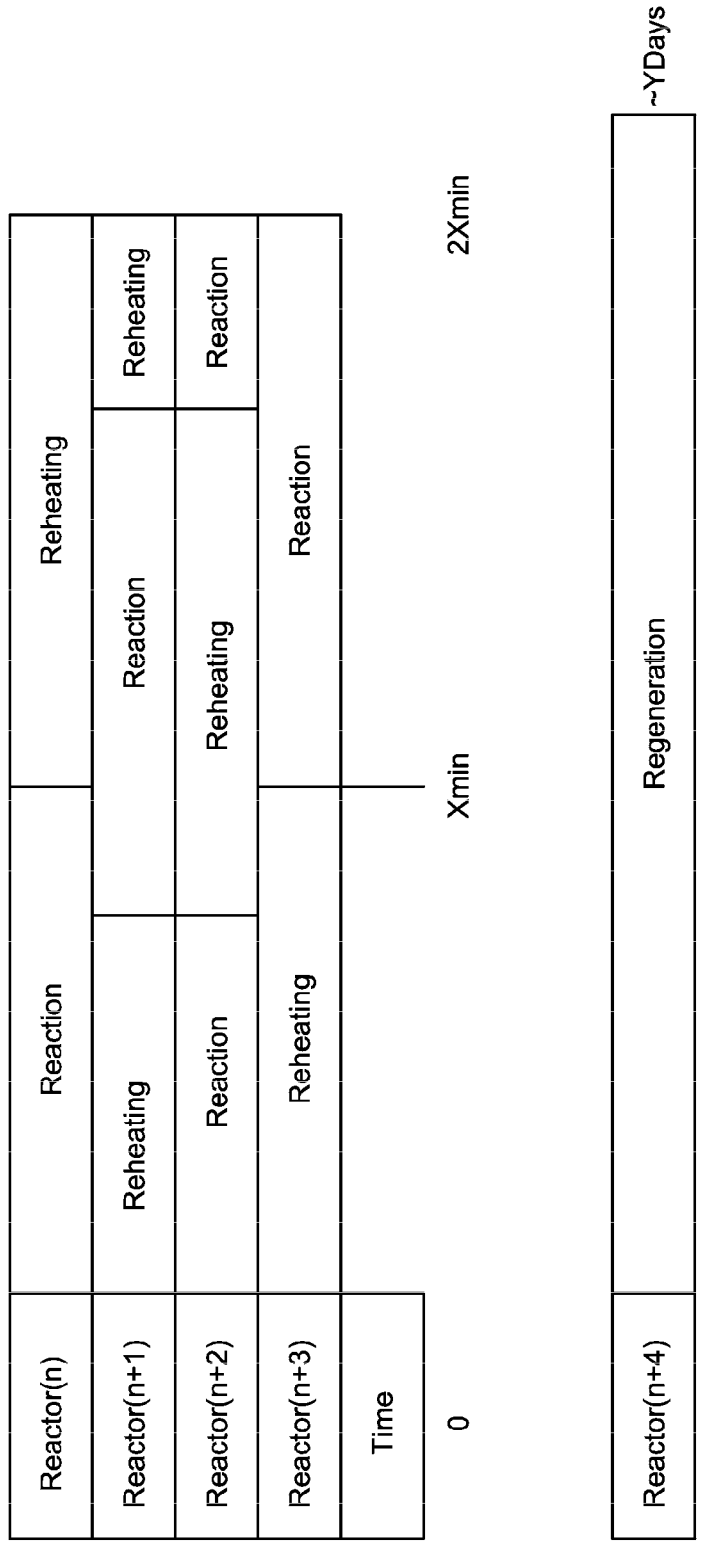
FIG. 1 shows an example time sequence for the reaction zones according to one embodiment of the invention.

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

As used herein, the term "about" refers to a range of values of plus or minus 10% of a specified value. For example, the phrase "about 200" includes plus or minus 10% of 200, or from 180 to 220.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as benzene. As used herein, the term aromatic encompasses compounds containing one or more aromatic rings, including, but not limited to, benzene, toluene, and xylene, and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene, and xylene, and polynuclear aromatics (PNAs), which include naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feedstock containing n-pentane, such as a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, Ni, Pd, and Pt.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

As used herein, the term "oxygen-containing" or "oxygen-containing compound" means oxygen and compounds containing oxygen, including but not limited to, $O_2$, $CO_2$, CO, $H_2O$, and oxygen-containing hydrocarbons such as alcohols, esters, ethers, etc.

The term "constraint index" is defined in U.S. Pat. No. 3,972,832 and U.S. Pat. No. 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types," Fifth edition, 2001, the entire content of which is incorporated herein by reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "carbon selectivity" means the moles of carbon in the respective cyclic $C_5$, CPD, $C_1$, and $C_{2-4}$ formed divided by total moles of carbon in the pentane converted. The phrase "a carbon selectivity to cyclic $C_5$ of at least 30%" means that 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the term "reactor system" refers to a system including one or more reactors and all necessary and optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reactions zones across multiple reactors. In other words and as is common, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where Umf is the minimum fluidizing velocity, Umb is the minimum bubbling velocity, Uc is the velocity at which fluctuation in pressure peaks and tr is transport velocity. These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010, which are incorporated herein by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$ in at least a portion of the reaction zone, and/or operating at a velocity higher than the minimum fluidization velocity while maintaining a gradient in gas and/or solid property (such as, temperature, gas, or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, $2^{nd}$ Edition, Butterworth-Heinemann, Boston, 1991, and Walas, S. M., Chapter 6 of *Chemical Process Equipment*, Revised $2^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid bed to another. Locus of minimum fluidization velocity is given in, for example, Kunii, D., Levenspiel, O., Chapter 3 of *Fluidization Engineering*, $2^{nd}$ Edition, Butterworth-Heinemann, Boston, 1991, and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, $2^{nd}$ Edition, Butterworth-Heinemann, Boston, 1991, and Walas, S. M., Chapter 6 of *Chemical Process Equipment*, Revised $2^{nd}$ Edition, Butterworth-Heinemann, Boston, 2010. A fluidized bed reactor, such as a circulating fluidized bed reactor, may be operated as a riser reactor.

As used herein, the term "fixed bed" or "packed bed" reactor refers to a zone or vessel (such as, vertical or horizontal, cylindrical pipe or a spherical vessel) and may include transverse (also known as cross flow), axial flow, and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors may be cyclically operated to have a reaction interval, a reheat interval, and/or a regeneration interval. The duration and/or order of the interval steps may change over time.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

"Average diameter" for particles in the range of 1 to 3500 μm is determined using a Mastersizer™ 3000 available from Malvern Instruments, Ltd., Worcestershire, England. Unless otherwise stated, particle size is determined at D50. D50 is the value of the particle diameter at 50% in the cumulative distribution. For example, if D50=5.8 um, then 50% of the particles in the sample are equal to or larger than 5.8 um and 50% are smaller than 5.8 um. (In contrast, if D90=5.8 um, then 10% of the particles in the sample are larger than 5.8 um and 90% are smaller than 5.8 um.) "Average diameter" for particles in the range of 3 mm to 50 mm is determined using a micrometer on a representative sample of 100 particles.

For purposes of the invention, 1 psi is equivalent to 6.895 kPa. Particularly, 1 psia is equivalent to 1 kPa absolute (kPa-a). Likewise, 1 psig is equivalent to 6.895 kPa gauge (kPa-g).

II. Acyclic $C_5$ Conversion Process

The first aspect of the invention is a process for conversion of an acyclic $C_5$ feedstock to a product comprising cyclic $C_5$ compounds (e.g., cyclopentadiene). The process comprises the steps of contacting said feedstock and, optionally, hydrogen under acyclic $C_5$ conversion conditions in the presence of one or more catalyst compositions, including but not limited to the catalyst compositions described herein, to form said product.

In one or more embodiments, the product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. In one or more embodiments, the cyclic $C_5$ compounds comprise at least about 20 wt %, or 30 wt %, or 40 wt %, or 70 wt % cyclopentadiene, or in the range of from about 10 wt % to about 80 wt %, alternately 20 wt % to 70 wt %.

In one or more embodiments, the acyclic $C_5$ conversion conditions include at least a temperature, an n-pentane partial pressure, and a weight hourly space velocity (WHSV). The temperature is in the range of about 400° C. to about 700° C., or in the range from about 450° C. to about 650° C., preferably, in the range from about 500° C. to about 600° C. The n-pentane partial pressure is in the range of about 3 to about 100 psia at the reactor inlet, or in the range from about 3 to about 50 psia, preferably, in the range from about 3 psia to about 20 psia. The weight hourly space velocity is in the range from about 1 to about 50 $hr^{-1}$, or in the range from about 1 to about 20 $hr^{-1}$. Such conditions include a molar ratio of the optional hydrogen co-feed to the acyclic $C_5$ feedstock in the range of about 0 to 3, or in the range from about 1 to about 2. Such conditions may also include co-feed $C_1$-$C_4$ hydrocarbons with the acyclic $C_5$ feed.

Preferably co-feed (if present), whether comprising hydrogen, $C_1$-$C_4$ hydrocarbons or both, is substantially free of oxygen-containing compounds. "Substantially free" used in this context means the co-feed comprises less than about 1.0 wt %, based upon the weight of the co-feed, e.g., less than about 0.1 wt %, less than about 0.01 wt %, less than about 0.001 wt %, less than about 0.0001 wt %, less than about 0.00001 wt % of oxygen-containing compounds.

In one or more embodiments, this invention relates to a process for conversion of n-pentane to cyclopentadiene comprising the steps of contacting n-pentane and, optionally, hydrogen (if present, typically $H_2$ is present at a ratio to n-pentane of 0.01 to 3.0) with one or more catalyst compositions, including but not limited to, the catalyst compositions described herein, to form cyclopentadiene at a temperature of 400° C. to 700° C., a partial pressure of n-pentane of 3 to about 100 psia at the reactor inlet, and a weight hourly space velocity of 1 to about 50 $hr^{-1}$.

In one or more embodiments, this invention relates to a process for converting $C_5$ hydrocarbons to cyclopentadiene in a reactor system, wherein the process comprises a reaction interval comprising: cyclically providing to the reactor system a feedstock comprising $C_5$ hydrocarbons; contacting the feedstock with a particulate material comprising a catalyst material in at least a first reaction zone under reaction conditions to convert at least a portion of the $C_5$ hydrocarbons to a first effluent comprising cyclopentadiene.

A. Reaction Interval i. Feedstock

During a reaction interval of the process, a feedstock comprising $C_5$ hydrocarbons, preferably an acyclic $C_5$ feedstock is provided to a reaction system along with a particulate material comprising a catalyst material. An acyclic $C_5$ feedstock useful herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the process of this invention comprises pentane, pentene, pentadiene, and mixtures of two or more thereof. Preferably, in one or more embodiments, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ feedstock, optionally, does not comprise $C_6$ aromatic compounds, such as benzene, preferably $C_6$ aromatic compounds are present at less than 5 wt %, preferably less than 1 wt %, preferably present at less than 0.01 wt %, preferably at 0 wt %.

The acyclic $C_5$ feedstock, optionally, does not comprise benzene, toluene, or xylene (ortho, meta, or para), preferably the benzene, toluene, or xylene (ortho, meta, or para) compounds are present at less than 5 wt %, preferably less than 1 wt %, preferably present at less than 0.01 wt %, preferably at 0 wt %.

The acyclic $C_5$ feedstock, optionally, does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %.

The acyclic $C_5$ feedstock, optionally, does not comprise $C_{6+}$ compounds, preferably $C_{6+}$ compounds are present at less than 5 wt %, preferably less than 1 wt %, preferably present at less than 0.01 wt %, preferably at 0 wt %.

Preferably, the $C_5$ feedstock is substantially free of oxygen-containing compounds. "Substantially free" used in this context means the feedstock comprises less than about 1.0 wt %, based upon the weight of the feed, e.g., less than about 0.1 wt %, less than about 0.01 wt %, less than about 0.001 wt %, less than about 0.0001 wt %, less than about 0.00001 wt % oxygen-containing compounds.

Preferably, an amount of the $C_5$ hydrocarbons (e.g., acyclic $C_5$ hydrocarbons) in the feedstock converted to cyclopentadiene is ≥about 5.0 wt %, ≥about 10.0 wt %, ≥about 20.0 wt %, ≥about 30.0 wt %, ≥about 40.0 wt %, ≥about 50.0 wt %, ≥about 60.0 wt %, ≥about 70.0 wt %, ≥about 80.0 wt %, or ≥about 90.0 wt %. Preferably, at least about 30.0 wt % or at least about 60.0 wt % of the $C_5$ hydrocarbons (e.g., acyclic $C_5$ hydrocarbons) is converted to cyclopentadiene. Ranges expressly disclosed include combinations of any of the above-enumerated values; e.g., about 5.0 wt % to about 90.0 wt %, about 10.0 wt % to about 80.0 wt %, about 20.0 wt % to about 70.0 wt %, about 20.0 wt % to about 60.0 wt %, etc. Preferably, about 20.0 wt % to about 90.0 wt % of the $C_5$ hydrocarbons (e.g., acyclic $C_5$ hydrocarbons) is converted to cyclopentadiene, more preferably about 30.0 wt % to about 85.0 wt %, more preferably about 40.0 wt % to about 80.0 wt %, about 45.0 wt % to about 75.0 wt %, or about 50.0 wt % to about 70.0 wt %.

Preferably, a hydrogen co-feedstock comprising hydrogen and, optionally, light hydrocarbons, such as $C_1$-$C_4$ hydrocarbons, is also fed into the first reactor. Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles. $C_1$-$C_4$ hydrocarbons may also be co-fed with the $C_5$.

ii. Reaction Zone

The feedstock is fed into a reactor system and contacted with a particulate material comprising a catalyst material in a reaction zone under reaction conditions to convert at least a portion of the $C_5$ hydrocarbons (e.g., acyclic $C_5$ hydrocarbons) to a first effluent comprising cyclopentadiene. The reaction zone may be a fluidized bed reactor or a fixed bed reactor, preferably a fixed bed reactor. The fixed bed reactor may be a vertical fixed bed or a horizontal fixed bed. Preferably, the vertical fixed bed is an axial flow vertical fixed bed or a radial flow fixed bed. Preferably, the horizontal fixed bed is a transverse flow horizontal fixed bed.

The reaction zone may include at least one internal structure to support the particulate material, to distribute feedstock uniformly, to collect hydrocarbon product, and/or reduce pressure drop within the reaction zone. For example, when the reaction zone is a vertical fixed bed, one or more internal structures, e.g., permeable concentric shells, may be included in the reaction zone to contain and support the particulate material, and the feedstock may be fed into a substantially open, center axis portion of the reaction zone and radially flow over the particulate material. Additionally or alternatively, a reaction zone may include at least one internal structure, preferably a plurality of internal structures (e.g., 2, 3, 4, 5, 6, 7, 8, 9, 10, 15, 20, 30, 40, 50, etc.). Examples of suitable internal structures include a plurality of support grids, hold down grids, baffles, sheds, trays, tubes, rods, and/or distributors.

During the reaction interval, a reaction zone is operated under reaction conditions sufficient to convert the feedstock (e.g., acyclic $C_5$ hydrocarbons) to cyclopentadiene. Preferably, the feedstock (e.g., acyclic $C_5$ hydrocarbons) may be fed to the reaction system at a weight hourly space velocity (WHSV, mass of acyclic $C_5$ hydrocarbons/mass of catalyst/hour) in the range of from about 1.0 to about 1000.0 $hr^{-1}$. The WHSV may be about 1.0 to about 900.0 $hr^{-1}$, about 1.0 to about 800.0 $hr^{-1}$, about 1.0 to about 700.0 $hr^{-1}$, about 1.0 to about 600.0 $hr^{-1}$, about 1.0 to about 500.0 $hr^{-1}$, about 1.0 to about 400.0 $hr^{-1}$, about 1.0 to about 300.0 $hr^{-1}$, about 1.0 to about 200.0 $hr^{-1}$, about 1.0 to about 100.0 $hr^{-1}$, about 1.0 to about 90.0 $hr^{-1}$, about 1.0 to about 80.0 $hr^{-1}$, about 1.0 to about 70.0 $hr^{-1}$, about 1.0 to about 60.0 $hr^{-1}$, about 1.0 to about 50.0 $hr^{-1}$, about 1.0 to about 40.0 $hr^{-1}$, about 1.0 to about 30.0 $hr^{-1}$, about 1.0 to about 20.0 $hr^{-1}$, about 1.0 to about 10.0 $hr^{-1}$, about 1.0 to about 5.0 $hr^{-1}$, about 2.0 to about 1000.0 $hr^{-1}$, about 2.0 to about 900.0 $hr^{-1}$, about 2.0 to about 800.0 $hr^{-1}$, about 2.0 to about 700.0 $hr^{-1}$, about 2.0 to about 600.0 $hr^{-1}$, about 2.0 to about 500.0 $hr^{-1}$, about 2.0 to about 400.0 $hr^{-1}$, about 2.0 to about 300.0 $hr^{-1}$, about 2.0 to about 200.0 $hr^{-1}$, about 2.0 to about 100.0 $hr^{-1}$, about 2.0 to about 90.0 $hr^{-1}$, about 2.0 to about 80.0 $hr^{-1}$, about 2.0 to about 70.0 $hr^{-1}$, about 2.0 to about 60.0 $hr^{-1}$, about 2.0 to about 50.0 $hr^{-1}$, about 2.0 to about 40.0 $hr^{-1}$, about 2.0 to about 30.0 $hr^{-1}$, about 2.0 to about 20.0 $hr^{-1}$, about 2.0 to about 10.0 $hr^{-1}$, and about 2.0 to about 5.0 $hr^{-1}$. Preferably, the WHSV is about 1.0 to about 100.0 $hr^{-1}$, more preferably about 1.0 to about 60.0 $hr^{-1}$, more preferably about 2.0 to about 40.0 $hr^{-1}$, more preferably about 2.0 to about 20.0 $hr^{-1}$.

Additionally, it may be preferable that a substantially inverse temperature profile be maintained in a reaction zone. As used herein, "inverse temperature profile" means that the reaction zone inlet temperature is lower than the reaction zone outlet temperature. Preferably, centerline temperature at the reaction zone inlet is lower than the centerline temperature at the reaction zone outlet. "Inverse temperature profile" includes systems where the temperature varies in the reaction zone so long as the temperature at the reaction zone inlet is lower than the temperature at the reaction zone outlet. "Inverse temperature profile" further encompasses a reaction zone having a centerline temperature T1; at some length along the reaction zone, the centerline temperature decreases to temperature T2; at a further length along the reaction zone, the centerline temperature rises to temperature T3; finally, the centerline temperature at the reaction zone outlet decreases to temperature T4; wherein T3>T4>T1>T2. The temperature measured where feedstock first contacts catalyst composition near the reactor inlet may be between about 0° C. to about 200° C., preferably, about 25° C. to about 150° C., more preferably about 50° C. to about 100° C., lower than the temperature measured where the effluent leaves contact with catalyst composition near the reactor outlet. Preferably, the reaction zone centerline temperature measured where feedstock first contacts catalyst composition near the reactor inlet may be between about 0° C. to about 200° C., preferably about 25° C. to about 150° C., more preferably about 50° C. to about 100° C., lower than the reaction zone centerline temperature measured where the effluent leaves contact with catalyst composition near the reactor outlet. In a preferred embodiment, the inverse temperature profile of a reaction zone means that temperature of the reaction zone increases from an inlet for the feedstock (e.g., acyclic $C_5$ hydrocarbons) to an outlet for an effluent. In other words, if the inlet for the feedstock is at a top portion of a reaction zone and the outlet for an effluent is at a bottom portion of the reaction zone, the temperature of the reaction zone may increase from a substantially top portion to a substantially bottom portion of the reaction zone; conversely, temperature of the reaction may decrease from a substantially bottom portion to a substantially top portion of the reaction zone. Maintaining an inverse temperature profile in the reaction zone may advantageously minimize carbonaceous material formation at the inlet, which can contribute to coking of the catalyst material. The inverse temperature profile may also provide sufficient reaction time and length in the reaction zone to produce a sufficient amount of Hz, at lower operating temperatures than outlet temperature, which can minimize carbonaceous material formation at the outlet for an effluent.

Alternatively, it may be preferable than an isothermal or substantially isothermal temperature profile be maintained in the reaction zone (e.g., in the reactor tubes). An advantage of maintaining an isothermal temperature may be increased catalyst efficiency and improved product yield by reducing the amount of low value, cracked (i.e., $C_{4-}$) byproduct. As used herein, "isothermal temperature profile" means that the temperature at each point between the reactor inlet and reactor outlet as measured along the tube centerline of the reactor is kept essentially constant, e.g., at the same temperature or within the same narrow temperature range wherein the difference between an upper temperature and a lower temperature is no more than about 40° C.; more preferably no more than about 20° C. Preferably, the isothermal temperature profile is one where the reactor inlet temperature is within about 40° C. of the reactor outlet temperature, alternately within about 20° C., alternately within about 10° C., alternately within about 5° C., alternately the reactor inlet temperature is the same as the reactor outlet temperature. Alternately, the isothermal temperature profile is one where the reactor inlet temperature is within about 20% of the reactor outlet temperature, alternately within about 10%, alternately within about 5%, alternately within about 1%.

Preferably, the isothermal temperature profile is one where the temperature along the length of the reaction zone(s) within the reactor does not vary by more than about 40° C. as compared to reactor inlet temperature, alternately not more than about 20° C., alternately not more than about 10° C., alternately not more than about 5° C. Alternately, the isothermal temperature profile is one where the temperature along the length of the reaction zone(s) within the reactor is within about 20% of the reactor inlet temperature, alternately within about 10%, alternately within about 5%, alternately within about 1% of the reactor inlet temperature.

Thus, the temperature of the feedstock (e.g., acyclic $C_5$ hydrocarbons) entering the reactor system at a feedstock inlet may be ≤about 700° C., ≤about 675° C., ≤about 650° C., ≤about 625° C., ≤about 600° C., ≤about 575° C., ≤about 550° C., ≤about 525° C., ≤about 500° C., ≤about 475° C., ≤about 450° C., ≤about 425° C., ≤about 400° C., ≤about 375° C., ≤about 350° C., ≤about 325° C., ≤about 300° C., ≤about 275° C., ≤about 250° C., ≤about 225° C. or ≤about 200° C. Preferably, the temperature of the feedstock (e.g., acyclic $C_5$ hydrocarbons) entering the reactor system is ≤about 550° C., more preferably ≤about 525° C., more preferably ≤about 500° C. Ranges of temperatures expressly disclosed include combinations of any of the above-enumerated values, e.g., about 200° C. to about 700° C., about 250° C. to about 600° C., about 350° C. to about 650° C., about 375° C. to about 500° C., etc. Preferably, the temperature of the feedstock (e.g., acyclic $C_5$ hydrocarbons) entering the reaction system is about 200° C. to about 700° C., more preferably about 300° C. to about 600° C., more preferably about 350° C. to about 550° C., more preferably about 375° C. to about 500° C. Providing the feedstock (e.g., acyclic $C_5$ hydrocarbons) at the above-described temperatures may advantageously minimize undesirable cracking of the $C_5$ hydrocarbons (e.g., acyclic $C_5$ hydrocarbons) before they can react in the presence of the catalyst material.

Additionally, the temperature of a first effluent exiting a reaction zone at an effluent outlet may be ≥about 400° C., ≥about 425° C., ≥about 450° C., ≥about 475° C., ≥about 500° C., ≥about 525° C., ≥about 550° C., ≥about 575° C., ≥about 600° C., ≥about 625° C., ≥about 650° C., ≥about 675° C., or ≥about 700° C. Preferably, the temperature of a first effluent exiting a reaction zone is ≥about 550° C., more preferably ≥about 575° C., more preferably ≥about 600° C. Ranges of temperatures expressly disclosed include combinations of any of the above-enumerated values, e.g., about 400° C. to about 700° C., about 475° C. to about 675° C., about 525° C. to about 650° C., about 550° C. to about 600° C., etc. Preferably, the temperature of a first effluent exiting the at least one first reaction zone is about 475° C. to about 700° C., more preferably about 500° C. to about 650° C., more preferably about 550° C. to about 625° C.

Additionally or alternatively, reaction conditions in a reaction zone may include a temperature (such as at the reactor centerline) of ≥about 300° C., ≥about 325° C., ≥about 350° C., ≥about 375° C., ≥about 400° C., ≥about 425° C., ≥about 450° C., ≥about 475° C., ≥about 500° C., ≥about 525° C., ≥about 550° C., ≥about 575° C., ≥about 600° C., ≥about 625° C., ≥about 650° C., ≥about 675° C., or ≥about 700° C. Additionally or alternatively, the temperature may be ≤about 300° C., ≤about 325° C., ≤about 350° C., ≤about 375° C., ≤about 400° C., ≤about 425° C., ≤about 450° C., ≤about 475° C., ≤about 500° C., ≤about 525° C., ≤about 550° C., ≤about 575° C., ≤about 600° C., ≤about 625° C., ≤about 650° C., ≤about 675° C., or ≤about 700° C. Ranges of temperatures expressly disclosed include combinations of any of the above-enumerated values, e.g., about 300° C. to about 1,000° C., about 350° C. to about 875° C., and about 400° C. to about 700° C., etc. Preferably, the temperature may be about 325° C. to about 700° C., more preferably about 400° C. to about 675° C., more preferably about 350° C. to about 650° C., more preferably about 450° C. to about 625° C. Optionally, a reaction zone may include one or more heating devices in order to maintain a temperature therein. Examples of suitable heating devices known in the art include, but are not limited to a fired tube, a heated coil with a high temperature heat transfer fluid, an electrical heater, and/or a microwave emitter.

Additionally or alternatively, reaction conditions in a reaction zone may include a pressure (e.g., outlet pressure) of ≤about 1.0 psia, ≤about 2.0 psia, ≤about 3.0 psia, ≤about 4.0, ≤about 5.0 psia, ≤about 10.0 psia, ≤about 15.0 psia, ≤about 20.0 psia, ≤about 25.0 psia, ≤about 30.0 psia, ≤about 35.0 psia, ≤about 40.0 psia, ≤about 45.0 psia, ≤about 50.0 psia, ≤about 55.0 psia, or ≤about 60.0 psia. Additionally or alternatively, the pressure may be ≥about 1.0 psia, ≥about 2.0 psia, ≥about 3.0 psia, ≥about 4.0 psia, ≥about 5.0 psia, ≥about 10.0 psia, ≥about 15.0 psia, ≥about 20.0 psia, ≥about 25.0 psia, ≥about 30.0 psia, ≥about 35.0 psia, ≥about 40.0 psia, ≥about 45.0 psia, ≥about 50.0 psia, ≥about 55.0 psia, or ≥about 60.0 psia. Ranges and combinations of temperatures and pressures expressly disclosed include combinations of any of the above-enumerated values, e.g., about 1.0 psia to about 60.0 psia, about 2.0 psia to about 50.0 psia, about 5.0 psia to about 35.0 psia, etc. Preferably, the pressure may be about 1.0 psia to about 60.0 psia, more preferably about 2.0 psia to about 40.0 psia, more preferably about 3.0 psia to about 30.0 psia, more preferably about 4.0 psia to about 15.0 psia, more preferably about 4.0 psia to about 10.0 psia. Additionally or alternatively, a pressure substantially at a feedstock inlet and/or substantially at an effluent outlet may be ≥about 0.5 psia, ≥about 1.0 psia, ≥about 2.0 psia, ≥about 3.0 psia, ≥about 4.0 psia, ≥about 5.0 psia, ≥about 10.0 psia, ≥about 14.0 psia, ≥about 15.0, psia ≥about 20.0 psia, ≥about 24.0 psia, ≥about 25.0 psia, ≥about 30.0 psia, ≥about 35.0 psia, ≥about 40.0 psia, ≥about 45.0 psia, or ≥about 50.0 psia. As understood herein, "at a feedstock inlet," "at an inlet," "at an effluent outlet," and "at an outlet" includes the space in and substantially around the inlet and/or outlet. Additionally or alternatively, a pressure substantially at an inlet of a feedstock (e.g., acyclic $C_5$ hydrocarbons) and/or substantially at an outlet of at least a first effluent may be ≤about 0.5 psia, ≤about 1.0 psia, ≤about 2.0 psia, ≤about 3.0 psia, ≤about 4.0 psia, ≤about 5.0 psia, ≤about 10.0 psia, ≤about 14.0 psia, ≤about 15.0 psia, ≤about 20.0 psia, ≤about 24.0 psia, ≤about 25.0 psia, ≤about 30.0 psia, ≤about 35.0 psia, ≤about 40.0 psia, ≤about 45.0 psia, or ≤about 50.0 psia. Ranges of pressures expressly disclosed include combinations of any of the above-enumerated values, e.g., about 0.5 psia to about 50.0 psia, about 5.0 psia to about 35.0 psia, about 1.0 psia to about 15.0 psia, etc. In particular, the pressure substantially at an inlet of a feedstock (inlet pressure) may be about 1.0 psia to about 20.0 psia, preferably about 4.0 psia to about 14.0 psia, more preferably about 4.0 psia to about 10.0 psia. The pressure substantially at an outlet of an effluent (outlet pressure) may be about 1.0 psia to about 50.0 psia, more preferably about 2.0 psia to about 40.0 psia, more preferably about 3.0 psia to about 30.0 psia, more preferably about 4.0 psia to about 14.0 psia, more preferably about 4.0 psia to about 10.0 psia.

Preferably, the pressure drop across the at least first reaction zone is low, e.g., at least about 0.1 psi, at least about 0.2 psi, at least about 0.3 psi, at least about 0.4 psi, at least about 0.5 psi, at least about 0.6 psi, at least about 0.7 psi, at least about 0.8 psi, at least about 0.9 psi, at least about 1.0 psi, at least about 1.5 psi, at least about 2.0 psi, at least about 4.0 psi, at least about 6.0 psi, at least about 8.0 psi, at least about 10.0 psi, at least about 12.0 psi, at least about 15.0 psi, at least about 20.0 psi, at least about 25 psi, or at least about 30 psi. Preferably, when the at least first reaction zone is a vertical fixed bed, the pressure drop across the at least first reaction zone is between about 0.3 to about 30.0 psi, more preferably about 0.4 to about 25.0 psi, more preferably about 0.5 to about 20.0 psi. When the at least first reaction zone is a horizontal fixed bed, the pressure drop across the at least first reaction zone is between about 0.1 to about 10.0 psi, more preferably about 0.1 to about 5.0 psi, more preferably about 0.2 to about 1.0 psi.

Additionally or alternatively, a stream comprising hydrogen may be fed to a reaction zone. Such a stream comprising hydrogen may be introduced into the reaction zone in order to minimize production of coke material on the particulate material and/or to fluidize the particulate material in the reaction zone. Such a stream comprising hydrogen may contain light hydrocarbons (e.g., $C_1$-$C_4$); preferably the content of light hydrocarbons is less than about 50 mol %, less than about 40 mol %, less than about 30 mol %, less than about 20 mol %, less than about 10 mol %, less than about 5 mol %, less than about 1 mol %. Preferably, the stream comprising hydrogen is substantially free of oxygen, e.g., less than about 1.0 wt %, less than about 0.1 wt %, less than about 0.01 wt %, less than about 0.001 wt %, less than about 0.0001 wt %, less than about 0.00001 wt %, etc.

iii Particulate Material

The reaction zone comprises a particulate material comprising a catalyst material (e.g., catalyst compositions) for promoting conversion of the $C_5$ hydrocarbons (e.g., acyclic $C_5$ hydrocarbons) to cyclopentadiene.

Catalyst compositions useful herein include microporous crystalline metallosilicates, such as crystalline aluminosilicates, crystalline ferrosilicates, or other metal-containing crystalline silicates (such as those where the metal or metal-containing compound is dispersed within the crystalline silicate structure and may or may not be a part of the crystalline framework. Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials), where one or more metals from Groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one or more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the crystalline metallosilicate has an Si/M molar ratio (where M is a group 8, 11, or 13 metal) greater than about 3, or greater than about 25, or greater than about 50, or greater than about 100, or greater than about 400, or in the range from about 100 to about 2,000, or from about 100 to about 1,500, or from about 50 to about 2,000, or from about 50 to about 1,200.

In one or more embodiments, the crystalline aluminosilicate has an $SiO_2/Al_2O_3$ molar ratio greater than about 3, or greater than about 25, or greater than about 50, or greater than about 100, or greater than about 400, or in the range from about 100 to about 400, or from about 100 to about 500, or from about 25 to about 2,000, or from about 50 to about 1,500, or from about 100 to 1,200, or from about 100 to about 1,000.

In another embodiment of the invention, the microporous crystalline metallosilicate (such as an aluminosilicate) is combined with a Group 10 metal or metal compound, and, optionally, one, two, three, or more Group 1, 2, or 11 metals or metal compounds.

In one or more embodiments, the Group 10 metal includes, or is selected from the group consisting of, Ni, Pd, and Pt, preferably Pt. The Group 10 metal content of said catalyst composition is at least 0.005 wt %, based on the weight of the catalyst composition. In one or more embodiments, the Group 10 content is in the range from about 0.005 wt % to about 10 wt %, or from about 0.005 wt % up to about 1.5 wt %, based on the weight of the catalyst composition.

In one or more embodiments, the Group 1 alkali metal includes, or is selected from the group consisting of, Li, Na, K, Rb, Cs, and mixtures of two or more thereof, preferably Na.

In one or more embodiments, the Group 2 alkaline earth metal is selected from the group consisting of Be, Mg, Ca, Sr, Ba, and mixtures of two or more thereof.

In one or more embodiments, the Group 1 alkali metal is present as an oxide and the metal is selected from the group consisting of Li, Na, K, Rb, Cs, and mixtures of two or more thereof. In one or more embodiments, the Group 2 alkaline earth metal is present as an oxide and the metal is selected from the group consisting of Be, magnesium, calcium, Sr, Ba, and mixtures of two or more thereof. In one or more embodiments, the Group 1 alkali metal is present as an oxide and the metal is selected from the group consisting of Li, Na, K, Rb, Cs, and mixtures of two or more thereof; and the Group 2 alkaline earth metal is present as an oxide and the metal is selected from the group consisting of Be, magnesium, calcium, Sr, Ba, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from about 0.005 wt % to about 10 wt %, or from about 0.005 wt % up to about 1.5 wt %, based on the weight of the catalyst composition.

In one or more embodiments, the catalyst composition has an Alpha Value (as measured prior to the addition of the Group 10 metal, preferably platinum) of less than 25, alternately less than 15, alternately from 1 to 25, alternately from 1.1 to 15. Alpha Value is determined as described in U.S. Pat. No. 3,354,078; The Journal of Catalysis, v. 4, p. 527, (1965); v. 6, p. 278 (1966): and v. 61, p. 395 (1980) using a constant temperature of 538° C. and a variable flow rate, as described in detail in The Journal of Catalysis, v. 61, p. 395, (1980).

In one or more embodiments of aluminosilicates, the molar ratio of said Group 1 alkali metal to Al is at least about 0.5, or from at least about 0.5 up to about 3, preferably at least about 1, more preferably at least about 2.

In one or more embodiments of aluminosilicates, the molar ratio of said Group 2 alkaline earth metal to Al is at least about 0.5, or from at least about 0.5 up to about 3, preferably at least about 1, more preferably at least about 2.

In one or more embodiments, the molar ratio of said Group 11 metal to Group 10 metal is at least about 0.1, or from at least about 0.1 up to about 10, preferably at least about 0.5, more preferably at least about 1. In one or more embodiments, the Group 11 alkaline earth metal is present as an oxide and the metal is selected from the group consisting of gold, silver, and copper, and mixtures of two or more thereof.

In one or more embodiments, the use of any one of the catalyst compositions of this invention provides a conversion of at least about 70%, or at least about 75%, or at least about 80%, or in the range from about 60% to about 80%, of said acyclic $C_5$ feedstock under acyclic $C_5$ conversion conditions of an n-pentane containing feedstock with equimolar $H_2$, a temperature in the range of about 550° C. to about 600° C., an n-pentane partial pressure between 3 and 10 psia, and an n-pentane weight hourly space velocity of 10 to 20 $hr^{-1}$.

In one or more embodiments, the use of any one of the catalyst compositions of this invention provides a carbon selectivity to cyclic $C_5$ compounds of at least about 30%, or at least about 40%, or at least about 50%, or in the range from about 30% to about 80%, under acyclic $C_5$ conversion conditions including an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

In one or more embodiments, the use of any one of the catalyst compositions of this invention provides a carbon selectivity to cyclopentadiene of at least about 30%, or at least about 40%, or at least about 50%, or in the range from about 30% to about 80%, under acyclic $C_5$ conversion conditions including an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and, more usually, particularly when the composite is prepared in the form of beads, extrudates, pills, oil drop formed particles, spray dried particles, etc., in the range of about 2 to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques, including high pressure hydrogen treatment and combustion of coke on the catalyst compositions with an oxygen-containing gas, such as air or $O_2$.

Useful catalyst compositions comprise a crystalline aluminosilicate or ferrosilicate, which is optionally combined with one, two, or more additional metals or metal compounds. Preferred combinations include:

1) a crystalline aluminosilicate (such as ZSM-5 or Zeolite L) combined with a Group 10 metal (such as Pt), a Group 1 alkali metal (such as sodium or potassium), and/or a Group 2 alkaline earth metal;

2) a crystalline aluminosilicate (such as ZSM-5 or Zeolite L) combined with a Group 10 metal (such as Pt) and a Group 1 alkali metal (such as sodium or potassium);

3) a crystalline aluminosilicate (such as a ferrosilicate or an iron treated ZSM-5) combined with a Group 10 metal (such as Pt), and a Group 1 alkali metal (such as sodium or potassium);

4) a crystalline aluminosilicate (Zeolite L) combined with a Group 10 metal (such as Pt) and a Group 1 alkali metal (such as potassium); and 5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a Group 10 metal (such as Ni, Pd, and Pt, preferably Pt) supported on silica (e.g., silicon dioxide) modified by a Group 1 alkali metal silicate (such as Li, Na, K, Rb, and/or Cs silicates) and/or a Group 2 alkaline earth metal silicate (such as Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica ($SiO_2$) may be any silica typically used as catalyst support such as those marketed under the tradenames of DAVISIL 646 (Sigma Aldrich), DAVISON 952, DAVISON 948, or DAVISON 955 (Davison Chemical Division of W.R. Grace and Company).

Catalyst composition shape and design are preferably configured to minimize pressure drop, increase heat transfer, and minimize mass transport phenomena. Suitable catalyst shape and design are described in WO 2014/053553, which is incorporated by reference in its entirety. The catalyst composition may be an extrudate with a diameter of 2 mm to 20 mm. Optionally, the catalyst composition cross section may be shaped with one or more lobes and/or concave sections. Additionally, the catalyst composition lobes and/or concave sections may be spiraled. The catalyst composition may be an extrudate with a diameter of 2 mm to 20 mm; and the catalyst composition cross section may be shaped with one or more lobes and/or concave sections; and the catalyst composition lobes and/or concave sections may be spiraled. For fixed bed reactors (fired tube, convective tube, and cyclic) lobed, concave, spiral, etc., particle shapes are particularly useful and for fluid bed reactors spherical particle shapes are particularly useful. Preferably, particles for a fixed bed (e.g., cyclic fixed bed reactor, fired tubes reactor, convectively heated tubes reactor, etc.) are typically an extrudate with a diameter of 2 mm to 20 mm; and the catalyst composition cross section may be shaped with one or more lobes and/or concave sections; and the catalyst composition lobes and/or concave sections may be spiraled.

For more information on useful catalyst compositions, please see applications:
1) U.S. Ser. No. 62/250,675, filed Nov. 4, 2015;
2) U.S. Ser. No. 62/250,681, filed Nov. 4, 2015;
3) U.S. Ser. No. 62/250,688, filed Nov. 4, 2015;
4) U.S. Ser. No. 62/250,695, filed Nov. 4, 2015; and
5) U.S. Ser. No. 62/250,689, filed Nov. 4, 2015, which are incorporated by reference herein.

Preferably, the catalyst material comprises platinum on ZSM-5, platinum on zeolite L, and/or platinum on silica.

Suitable amounts of catalyst material in the particulate material (e.g., first particulate material, second particulate material) may be ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, ≤about 99.0 wt % or about 100.0 wt %. Preferably, the particulate material may comprise ≤about 25.0 wt % catalyst material. Additionally or alternatively, the particulate material (e.g., first particulate material, second particulate material) may comprise the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, or ≥about 95.0 wt %. Ranges expressly disclosed include combinations of any of the above-enumerated values; e.g., about 1.0 wt % to about 100.0 wt %, about 5.0 wt % to about 100.0 wt %, about 10.0 wt % to about 90.0 wt %, about 20.0 wt % to about 80.0 wt %, etc. Preferably, the particulate material (e.g., first particulate material, second particulate material) may comprise the catalyst material in an amount of about 1.0 wt % to about 100.0 wt %, more preferably about 5.0 wt % to about 100.0 wt %, more preferably about 25.0 wt % to about 100.0 wt %, more preferably about 50.0 wt % to about 100.0 wt %, more preferably about 10.0 wt % to about 75.0 wt %, more preferably about 20.0 wt % to about 70.0 wt, more preferably about 70.0 wt % to about 100.0 wt %.

In various aspects, the particulate material (e.g., first particulate material, second particulate material) may further comprise one or more inert materials. As referred to herein, the inert material is understood to include materials which promote a negligible amount (e.g., ≤about 3%, ≤about 2%, ≤about 1%, etc.) of conversion of the feedstock intermediate products, or final products under the reaction conditions described herein. The catalyst material and the inert material may be combined as portions of the same particles and/or may be separate particles.

Catalyst composition shape and design are preferably configured to minimize pressure drop, increase heat transfer, and minimize mass transport phenomena. Catalyst composition may be formed into particles that are randomly loaded into the reactor or may be structured catalyst shapes within the reactor.

Suitable catalyst particle shapes and designs are described in WO 2014/053553, which is incorporated herein by reference. The catalyst composition may be an extrudate with a diameter of 2 mm to 20 mm, for example, 2 mm to 10 mm, or 5 mm to 15 mm. Optionally, the catalyst composition cross section may be shaped with one or more lobes and/or concave sections. Additionally, the catalyst composition lobes and/or concave sections may be spiraled. Shapes may also include holes or perforations in the shapes to increase voltage and improve mass transfer.

Structured catalyst shape examples are coating of catalyst onto the inner wall of the reactor and onto formed inorganic support structures (metallic and ceramic preferred ceramics are those with high thermal conductivity, such as silicon carbide, aluminum nitride, boron carbide, and silicon nitride). Formed inorganic support structures may be ordered structures, such as extruded ceramic monoliths and extruded or rolled metal monoliths. Formed inorganic support structures may also include ceramic or metal foams and 3D printed structures.

Additionally, the catalyst material and/or inert material may be essentially spherical (i.e., <about 20%, <about 30%, <about 40%, <about 50% aberration in diameter), cylindrical or lobed shaped.

Suitable amounts of inert material in the particulate material may be about 0.0 wt %, ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, or ≥about 99.0 wt %. Preferably, the particulate material may comprise ≥about 25.0 wt % inert material. Additionally or alternatively, the particulate material may comprise an inert material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, or ≤about 99.0 wt %. Ranges expressly disclosed include combinations of any of the above-enumerated values, e.g., about 0.0 wt % to about 99.0 wt %, about 0.0 wt % to about 95.0 wt %, about 10.0 wt % to about 90.0 wt %, about 20.0 wt % to about 80.0 wt %, etc. Preferably, the particulate material may comprise an inert material in an amount of about 0.0 wt % to about 95.0 wt %, more preferably about 25.0 wt % to about 90.0 wt %, more preferably about 30.0 wt % to about 80.0 wt %.

In various aspects, for fixed bed operation, the catalyst material and/or the inert material (either as separate particles or as combined as portions of the same particles) may have an average diameter of ≥about 0.1 mm, ≥about 0.5 mm, ≥about 1 mm, ≥about 2 mm, ≥about 3 mm, ≥about 4 mm, ≥about 5 mm, ≥about 6 mm, ≥about 7 mm, ≥about 8 mm, ≥about 9 mm, ≥about 10 mm, ≥about 12 mm, ≥about 14 mm, ≥about 16 mm, ≥about 18 mm, ≥about 20 mm, ≥about 22 mm, ≥about 24 mm, ≥about 26 mm, ≥about 28 mm, ≥about 30 mm, ≥about 35 mm, ≥about 40 mm, ≥about 45 mm, or ≥about 50 mm. Additionally or alternatively, the catalyst material and/or the inert material (either as separate particles or as combined as portions of the same particles) may have an average diameter of ≤about 0.1 mm, ≤about 0.5 mm, ≤about 1 mm, ≤about 2 mm, ≤about 3 mm, ≤about 4 mm, ≤about 5 mm, ≤about 6 mm, ≤about 7 mm, ≤about 8 mm, ≤about 9 mm, ≤about 10 mm, ≤about 12 mm, ≤about 14 mm, ≤about 16 mm, ≤about 18 mm, ≤about 20 mm, ≤about 22 mm, ≤about 24 mm, ≤about 26 mm, ≤about 28 mm, ≤about 30 mm, ≤about 35 mm, ≤about 40 mm, ≤about 45 mm, or ≤about 50 mm. Ranges expressly disclosed include combinations of any of the above-enumerated values, e.g., about 0.1 mm to about 50 mm, about 1 mm to about 35 mm, about 2 mm to about 30 mm, about 3 mm to about 40 mm, etc. Preferably, the catalyst material and/or the inert material (either as separate particles or as combined as portions of the same particles) may have an average diameter of about 0.5 mm to about 30 mm, more preferably about 1 mm to about 20 mm, more preferably about 2 mm to about 10 mm, more preferably about 3 mm to about 8 mm.

In various aspects, for captive fluidized bed operation, the catalyst material and/or the inert material (either as separate particles or as combined as portions of the same particles) may have an average diameter of ≥about 50 μm, ≥about 100 μm, ≥about 200 μm, ≥about 300 μm, ≥about 400 μm, ≥about 500 μm, ≥about 600 μm, ≥about 700 μm, ≥about 800 μm, ≥about 900 μm, ≥about 1000 μm, ≥about 1100 μm, ≥about 1200 μm, ≥about 1300 μm, ≥about 1400 μm, ≥about 1500 μm, ≥about 1600 μm, ≥about 1700 μm, ≥about 1800 μm, ≥about 1900 μm, ≥about 2000 μm, ≥about 2100 μm, ≥about 2200 μm, ≥about 2300 μm, ≥about 2400 μm, ≥about 2500 μm, ≥about 2600 μm, ≥about 2700 μm, ≥about 2800 μm, ≥about 2900 μm, ≥about 3000 μm, ≥about 3100 μm, ≥about 3200 μm, ≥about 3300 μm, ≥about 3400 μm, ≥about 3500 μm, ≥about 3600 μm, ≥about 3700 μm, ≥about 3800 μm, ≥about 3900 μm, ≥about 4000 μm, ≥about 4100 μm, ≥about 4200 μm, ≥about 4300 μm, ≥about 4400 μm, ≥about 4500 μm, ≥about 5000 μm, ≥about 5500 μm, ≥about 6000 μm, ≥about 6500 μm, ≥about 7000 μm, ≥about 7500 μm, ≥about 8000 μm, ≥about 8500 μm, ≥about 9000 μm, ≥about 9500 μm, or ≥about 10,000 μm. Additionally or alternatively, for captive fluidized bed operation, the catalyst material and/or the inert material (either as separate particles or as combined as portions of the same particles) may have an average diameter of ≤about 50 μm, ≤about 100 μm, ≤about 200 μm, ≤about 300 μm, ≤about 400 μm, ≤about 500 μm, ≤about 600 μm, ≤about 700 μm, ≤about 800 μm, ≤about 900 μm, ≤about 1000 μm, ≤about 1100 μm, ≤about 1200 μm, ≤about 1300 μm, ≤about 1400 μm, ≤about 1500 μm, ≤about 1600 μm, ≤about 1700 μm, ≤about 1800 μm, ≤about 1900 μm, ≤about 2000 μm, ≤about 2100 μm, ≤about 2200 μm, ≤about 2300 μm, ≤about 2400 μm, ≤about 2500 μm, ≤about 2600 μm, ≤about 2700 μm, ≤about 2800 μm, ≤about 2900 μm, ≤about 3000 μm, ≤about 3100 μm, ≤about 3200 μm, ≤about 3300 μm, ≤about 3400 μm, ≤about 3500 μm, ≤about 3600 μm, ≤about 3700 μm, ≤about 3800 μm, ≤about 3900 μm, ≤about 4000 μm, ≤about 4100 μm, ≤about 4200 μm, ≤about 4300 μm, ≤about 4400 μm, ≤about 4500 μm, ≤about 5000 μm, ≤about 5500 μm, ≤about 6000 μm, ≤about 6500 μm, ≤about 7000 μm, ≤about 7500 μm, ≤about 8000 μm, ≤about 8500 μm, ≤about 9000 μm, ≤about 9500 μm, or ≤about 10,000 μm. Ranges expressly disclosed include combinations of any of the above-enumerated values, e.g., about 50 μm to about 10,000 μm, about 100 μm to about 9000 μm, about 200 μm to about 7500 μm, about 200 μm to about 5500 μm, about 100 μm to about 4000 μm, about 100 μm to about 700 μm, etc. Preferably, in a fast fluidized bed, the catalyst material and/or the inert material (either as separate particles or as combined as portions of the same particles) may have an average diameter of about 100 μm to about 4000 μm, more preferably about 100 μm to about 700 μm, more preferably about 100 μm to about 600 μm, more preferably about 100 μm to about 500 μm. Preferably, in an ebulatting fluidized bed, the catalyst material and/or the inert material (either as separate particles or as combined as portions of the same particles) may have an average diameter of about 1000 μm to about 10,000 μm, more preferably about 2000 μm to about 8000 μm, more preferably about 3000 μm to about 6000 μm, more preferably about 3500 μm to about 4500 μm.

Preferably, the particulate material (e.g., thermal energy stored in the particulate material) provides at least a portion of the heat required for increasing sensible heat of the feedstock and/or converting at least a portion of the acyclic $C_5$ hydrocarbons to the first effluent comprising cyclopentadiene. For example, the particulate material may provide ≥about 30%, ≥about 35%, ≥about 40%, ≥about 45%, ≥about 50%, ≥about 55%, ≥about 60%, ≥about 65%, ≥about 70%, ≥about 75%, ≥about 80%, ≥about 85%, ≥about 90%, ≥about 95%, or about 100% of the heat required. Preferably, the particulate material may provide ≥about 50% of the heat required for converting at least a portion of the acyclic $C_5$ hydrocarbons to the first effluent comprising cyclopentadiene. Ranges expressly disclosed include combinations of any of the above-enumerated values; e.g., about 30% to about 100%, about 40% to about 95%, about 50% to about 90%, etc. Preferably, the particulate material may provide about 30% to about 100% of the heat required, more preferably 50% to about 100% of the heat required, more preferably 70% to about 100% of the heat required.

Additionally or alternatively, for captive fluidized bed operation, fresh particulate material may be provided directly to a reaction zone on an as needed basis to make up for catalyst losses due to physical degradation (i.e., attrition and loss of fines from the reactor) or catalyst performance deterioration due to aging.

iv. Effluent

An effluent (e.g., first effluent, second effluent) exiting a reaction zone during the reaction interval may comprise a variety of hydrocarbon compositions produced from the reaction of the $C_5$ hydrocarbons (e.g., acyclic $C_5$ hydrocarbons) in the reaction zone. The hydrocarbon compositions typically have mixtures of hydrocarbon compounds having from 1 to 30 carbon atoms ($C_1$-$C_{30}$ hydrocarbons), from 1 to 24 carbon atoms ($C_1$-$C_{24}$ hydrocarbons), from 1 to 18 carbon atoms ($C_1$-$C_{18}$ hydrocarbons), from 1 to 10 carbon atoms ($C_1$-$C_{10}$ hydrocarbons), from 1 to 8 carbon atoms ($C_1$-$C_8$ hydrocarbons), and from 1 to 6 carbon atoms ($C_1$-$C_6$ hydrocarbons). Particularly, an effluent comprises cyclopentadiene. The cyclopentadiene may be present in a hydrocarbon portion of an effluent (e.g., first effluent, second effluent) in an amount of ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, or ≥about 80.0 wt %. Additionally or alternatively, the cyclopentadiene may be present in a hydrocarbon portion of an effluent (e.g., first effluent, second effluent) in an amount of ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, or ≤about 85.0 wt %. Ranges expressly disclosed include combinations of any of the above-enumerated values, e.g., about 20.0 wt % to about 85.0 wt %, about 30.0 wt % to about 75.0 wt %, about 40.0 wt % to about 85.0 wt %, about 50.0 wt % to about 90.0 wt %, etc. Preferably, the cyclopentadiene may be present in a hydrocarbon portion of an effluent (e.g., first effluent, second effluent) in an amount of about 10.0 wt % to about 85.0 wt %, more preferably about 25.0 wt % to about 80.0 wt %, more preferably about 40.0 wt % to about 75.0 wt %.

In other aspects, an effluent (e.g., first effluent, second effluent) may comprise one or more other $C_5$ hydrocarbons in addition to cyclopentadiene. Examples of other $C_5$ hydrocarbons include, but are not limited to, cyclopentane and cyclopentene. The one or more other $C_5$ hydrocarbons may be present in a hydrocarbon portion of an effluent (e.g., first effluent, second effluent) in an amount of ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, or ≥about 70.0 wt %. Additionally or alternatively, the one or more other $C_5$ hydrocarbons may be present in a hydrocarbon portion of an effluent (e.g., first effluent, second effluent) in an amount of ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, or ≤about 70.0 wt %. Ranges expressly disclosed include combinations of any of the above-enumerated values, e.g., about 10.0 wt % to about 70.0 wt %, about 10.0 wt % to about 55.0 wt %, about 15.0 wt % to about 60.0 wt %, about 25.0 wt % to about 65.0 wt %, etc. Preferably, the one or more other $C_5$ hydrocarbons may be present in a hydrocarbon portion of an effluent (e.g., first effluent, second effluent) in an amount of about 30.0 wt % to about 65.0 wt %, more preferably about 20.0 wt % to about 40.0 wt %, more preferably about 10.0 wt % to about 25.0 wt %.

In other aspects, an effluent (e.g., first effluent, second effluent) may also comprise one or more aromatics, e.g., having 6 to 30 carbon atoms, particularly 6 to 18 carbon atoms. The one or more aromatics may be present in a hydrocarbon portion of an effluent (e.g., first effluent, second effluent) in an amount of about ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, or ≥about 65.0 wt %. Additionally or alternatively, the one or more aromatics may be present in a hydrocarbon portion of an effluent (e.g., first effluent, second effluent) in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, or ≤about 65.0 wt %. Ranges expressly disclosed include combinations of any of the above-enumerated values, e.g., about 1.0 wt % to about 65.0 wt %, about 10.0 wt % to about 50.0 wt %, about 15.0 wt % to about 60.0 wt %, about 25.0 wt % to about 40.0 wt %, etc. Preferably, the one or more aromatics may be present in a hydrocarbon portion of an effluent (e.g., first effluent, second effluent) in an amount of about 1.0 wt % to about 15.0 wt %, more preferably about 1.0 wt % to about 14.0 wt %, more preferably about 1.0 wt % to about 5.0 wt %.

For information on possible dispositions of the effluents, please see applications:
1) U.S. Ser. No. 62/250,678, filed Nov. 4, 2015;
2) U.S. Ser. No. 62/250,692, filed Nov. 4, 2015;
3) U.S. Ser. No. 62/250,702, filed Nov. 4, 2015; and
4) U.S. Ser. No. 62/250,708, filed Nov. 4, 2015; which are incorporated herein by reference.

v. Reaction Interval Duration

Preferably, the reaction interval may have a duration of ≥about 1 min, ≥about 2 min, ≥about 3 min, ≥about 4 min, ≥about 5 min, ≥about 6 min, ≥about 7 min, ≥about 8 min, ≥about 9 min, ≥about 10 min, ≥about 15 min, ≥about 20 min, ≥about 25 min, ≥about 30 min, ≥about 35 min, ≥about 40 min, ≥about 45 min, ≥about 50 min, ≥about 55 min, ≥about 60 min, ≥about 65 min, ≥about 70 min, ≥about 75 min, ≥about 80 min, ≥about 85 min, ≥about 90 min, ≥about 95 min, ≥about 100 min, ≥about 110 min, or ≥about 120 min.

Additionally or alternatively, the reaction interval may have a duration of ≤about 1 min, ≤about 2 min, ≤about 3 min, ≤about 4 min, ≤about 5 min, ≤about 6 min, ≤about 7 min, ≤about 8 min, ≤about 9 min, ≤about 10 min, ≤about 15 min, ≤about 20 min, ≤about 25 min, ≤about 30 min, ≤about 35 min, ≤about 40 min, ≤about 45 min, ≤about 50 min, ≤about 55 min, ≤about 60 min, ≤about 65 min, ≤about 70 min, ≤about 75 min, ≤about 80 min, ≤about 85 min, ≤about 90 min, ≤about 95 min, ≤about 100 min, ≤about 110 min, or ≤about 120 min. Ranges expressly disclosed include combinations of any of the above-enumerated values, e.g., about 1 to about 120 min, about 1 to about 90 min, about 4 to about 80 min, about 10 to about 75 min, etc. Preferably, the reaction interval may have a duration of about 1 to about 120 min, more preferably about 1 to about 90 min, more preferably about 1 to about 60 min, more preferably about 1 to about 40 min, more preferably about 1 to about 15 min, more preferably about 1 to about 10 min, more preferably about 2 to about 8 min.

Additionally or alternatively, the reaction interval may be performed until the temperature in a reaction zone is ≤about 300° C., ≤about 325° C., ≤about 350° C., ≤about 375° C., ≤about 400° C., ≤about 425° C., ≤about 450° C., ≤about 475° C., ≤about 500° C., ≤about 525° C., ≤about 550° C., ≤about 575° C., ≤about 600° C., ≤about 650° C. or ≤about 675° C. Ranges expressly disclosed include combinations of any of the above-enumerated values, e.g., about 300° C. to about 675° C., about 400° C. to about 600° C., about 425° C. to about 575° C., etc. Preferably, the reaction interval may be performed until the temperature in a reaction zone falls below about 400° C., below about 450° C., below about 475° C., below about 500° C., below about 550° C., below about 575° C., or below about 600° C.

vi. Separation of the Effluent

In various aspects, the particulate material may become entrained with hydrocarbons (e.g., cyclopentadiene) in the effluent (e.g., first effluent, second effluent) as the effluent travels through and/or exits a reaction zone. Thus, the process may further comprise separating particulate material, which may be entrained with hydrocarbons (e.g., cyclopentadiene) in the effluent (e.g., first effluent, second effluent). This separating may comprise removal of the particulate material from the hydrocarbons (e.g., cyclopentadiene) by any suitable means, such as, but not limited to cyclones, filter, electrostatic precipitators, heavy liquid contacting, and/or other gas solid separation equipment, which may be inside and/or outside the at least one reaction zone. The effluent free of particulate material may then travel to a product recovery system. Additionally, the removed particulate material may then be fed back into the at least one reaction zone, for example, in a substantially top portion of the at least one reaction zone using known methods.

B. Reheating Interval

During the reaction interval, the particulate material may cool, i.e., reduce temperature. Further, coke material may form on the particulate material, particularly on the catalyst material, which may reduce the activity of the catalyst material. This catalyst material at the end of a reaction interval with coke formation and/or having a reduced temperature is referred to as a "spent catalyst material."

Thus, the process may further comprise a reheating interval where the feedstock at a reaction zone may be cyclically halted and a reheating gas may be provided to the reaction zone to the reactor system to reheat the particulate material. The reheating gas may comprise an inert substance (e.g., $N_2$, CO), methane, and/or hydrogen. In various aspects, the reheating gas may comprise an inert substance and may be fed a reaction zone to reheat the particulate material. Additionally or alternatively, the reheating gas may comprise hydrogen and the reheating gas may contact the particulate material (e.g., spent catalyst material) to remove at least a portion of incrementally deposited coke material on the catalyst material thereby forming a rejuvenated catalyst material and volatile hydrocarbon, such as, but not limited to, methane. As used herein, the term "incrementally deposited" coke material refers to an amount of coke material that is deposited on the catalyst material during each reaction interval as opposed to a cumulative amount of coke material deposited on the catalyst material during multiple reaction intervals. Preferably, the reheating gas comprising hydrogen is substantially free of oxygen, which can damage and/or reduce activity of the catalyst material. Preferably, the reheating gas comprises hydrogen and is substantially free of reactive oxygen-containing compounds. "Substantially free" used in this context means the reheating gas comprises less than about 1.0 wt %, based upon the weight of the rejuvenation stream, e.g., less than about 0.1 wt %, less than about 0.01 wt %, less than about 0.001 wt %, less than about 0.0001 wt %, less than about 0.00001 wt % oxygen-containing compounds. "Reactive oxygen-containing compounds" are compounds where the oxygen is available to react with the catalyst as compared to inert compounds containing oxygen (such as CO), which do not react with the catalyst. Preferably the reheating gas comprises ≥50 wt % $H_2$, such as ≥60 wt %, ≥70 wt %, preferably ≥90 wt % $H_2$ and may further comprise an inert substance (e.g., $N_2$, CO), and/or methane. After a suitable duration, the reheating gas and, optionally, the volatile hydrocarbon, may exit a reaction zone via an outlet.

In various aspects, the reheating gas may flow in a direction co-current or counter-current to a direction of a flow of the feedstock. For example, if the feedstock enters at a top portion of a reaction zone during a reaction interval, during the reheating interval, the reheating gas may also enter at a top portion of a reaction zone and thereby flow in a direction co-current to a direction of flow of the feedstock. Additionally or alternatively, if the feedstock enters at a top portion of a reaction zone, during the reheating interval, the reheating gas may enter at a bottom portion of a reaction zone and thereby flow in a direction counter-current to a direction of flow of the feedstock. Preferably, the reheating gas flows in a direction counter-current to a direction of flow of the feedstock and/or an inverse temperature profile in the reaction zone may be achieved.

The reheating gas may enter a reaction zone and/or the reheating interval may be operated at a temperature of ≥about 400° C., ≥about 450° C., ≥about 500° C., ≥about 550° C., ≥about 600° C., ≥650° C., ≥about 700° C., ≥750° C., ≥about 800° C., ≥850° C., or ≥about 900° C. Preferably, the reheating gas may enter a reaction zone and/or the reheating interval may be operated at a temperature of ≥about 600° C. Additionally or alternatively, the reheating gas may enter a reaction zone and/or the reheating interval may be operated at a temperature of ≤about 400° C., ≤about 450° C., ≤about 500° C., ≤about 550° C., ≤about 600° C., ≤650° C., ≤about 700° C., ≤about 750° C., ≤about 800° C., ≤about 850° C., or ≤about 900° C. Ranges of temperatures expressly disclosed include combinations of any of the above-enumerated values, e.g., about 400° C. to about 900° C., about 450° C. to about 850° C., about 500° C. to about 800° C., etc. Preferably, the reheating gas may enter a reaction zone and/or the reheating interval may be operated at a temperature of about 400° C. to about 800° C., more preferably about 600° C. to about 800° C., more preferably about 625° C. to about 700° C., more preferably about 550° C. to about 750° C.

Additionally or alternatively, the reheating gas may enter a reaction zone and/or the reheating interval may be operated at a pressure of ≥about 1.0 psia, ≥about 5.0 psia, ≥about 25.0 psia, ≥about 50.0 psia, ≥about 75.0 psia, ≥about 100.0 psia, ≥about 125.0 psia, ≥about 150.0 psia, ≥about 175.0 psia, ≥about 200.0 psia, ≥about 225.0 psia, ≥about 250.0 psia, ≥about 275.0 psia, ≥about 300.0 psia, ≥about 325.0 psia, or ≥about 350.0 psia. Preferably, the reheating gas may enter a reaction zone and/or the reheating interval may be operated at a pressure of ≥about 100.0 psia. Additionally or alternatively, the reheating gas may enter a reaction zone and/or the reheating interval may be operated at a pressure of ≤about 1.0 psia, ≤about 5.0 psia, ≤about 25.0 psia, ≤about 50.0 psia, ≤about 75.0 psia, ≤about 100.0 psia, ≤about 125.0 psia, ≤about 150.0 psia, ≤about 175.0, psia ≤about 200.0 psia, ≤about 225.0 psia, ≤about 250.0 psia, ≤about 275.0 psia, ≤about 300.0 psia, ≤about 325.0 psia, or ≤about 350.0 psia. Ranges of pressures expressly disclosed include combinations of any of the above-enumerated values, e.g., about 1.0 psia to about 350.0 psia, about 5.0 psia to about 275.0 psia, about 25.0 psia to about 250.0 psia, etc. In particular, the reheating gas may enter a reaction zone and/or the reheating interval may be operated at a pressure of about 1 psia to about 300 psia, more preferably about 5 psia to about 250 psia, more preferably about 25 psia to about 250 psia.

Preferably, during the reheating interval, the incrementally deposited coke material is removed from the catalyst material in an amount of ≥about 1.0 wt %, ≥about 5.0 wt %, ≥about 10.0 wt %, ≥about 15.0 wt %, ≥about 20.0 wt %, ≥about 25.0 wt %, ≥about 30.0 wt %, ≥about 35.0 wt %, ≥about 40.0 wt %, ≥about 45.0 wt %, ≥about 50.0 wt %, ≥about 55.0 wt %, ≥about 60.0 wt %, ≥about 65.0 wt %, ≥about 70.0 wt %, ≥about 75.0 wt %, ≥about 80.0 wt %, ≥about 85.0 wt %, ≥about 90.0 wt %, ≥about 95.0 wt %, ≥about 99.0 wt %, or about 100.0 wt %. Preferably, at least about 10.0 wt % of the incrementally deposited coke material is removed from the catalyst material, more preferably at least about 90.0 wt %, more preferably at least about 95.0 wt %, more preferably at least about 99.0 wt %. Additionally or alternatively, the incrementally deposited coke material is removed from the catalyst material in an amount of ≤about 1.0 wt %, ≤about 5.0 wt %, ≤about 10.0 wt %, ≤about 15.0 wt %, ≤about 20.0 wt %, ≤about 25.0 wt %, ≤about 30.0 wt %, ≤about 35.0 wt %, ≤about 40.0 wt %, ≤about 45.0 wt %, ≤about 50.0 wt %, ≤about 55.0 wt %, ≤about 60.0 wt %, ≤about 65.0 wt %, ≤about 70.0 wt %, ≤about 75.0 wt %, ≤about 80.0 wt %, ≤about 85.0 wt %, ≤about 90.0 wt %, ≤about 95.0 wt %, ≤about 99.0 wt %, or about 100.0 wt %. Ranges expressly disclosed include combinations of any of the above-enumerated values, e.g., about 1.0 wt % to about 100.0 wt %, about 5.0 wt % to about 95.0 wt %, about 10.0 wt % to about 90.0 wt %, about 30.0 wt % to about 90.0 wt %, etc. Preferably, the incrementally deposited coke material is removed from the catalyst material in an amount of about 1.0 wt % to about 100.0 wt %, more preferably about 10.0 wt % to about 100.0 wt %, more preferably about 90.0 wt % to about 100.0 wt %, more preferably about 95.0 wt % to about 100.0 wt %.

In various aspects, the temperature of the rejuvenated catalyst material may be ≥about 400° C., ≥about 450° C., ≥about 500° C., ≥about 550° C., ≥about 600° C., ≥about 650° C., ≥about 700° C., ≥about 750° C., ≥about 800° C., ≥about 850° C., or ≥about 900° C. Additionally or alternatively, the temperature of the rejuvenated catalyst material may be ≤about 400° C., ≤about 450° C., ≤about 500° C., ≤about 550° C., ≤about 600° C., ≤about 650° C., ≤about 700° C., ≤about 750° C., ≤about 800° C., ≤about 850° C., or ≤about 900° C. Ranges of temperatures expressly disclosed include combinations of any of the above-enumerated values, e.g., about 400° C. to about 900° C., about 450° C. to about 850° C., about 500° C. to about 800° C., etc. Preferably, the temperature of the rejuvenated catalyst material may be about 400° C. to about 800° C., more preferably about 600° C. to about 800° C., more preferably about 550° C. to about 750° C.

Preferably, the reheating interval may have a duration of ≥about 1 min, ≥about 5 min, ≥about 10 min, ≥about 15 min, ≥about 20 min, ≥about 25 min, ≥about 30 min, ≥about 35 min, ≥about 40 min, ≥about 45 min, ≥about 50 min, ≥about 55 min, ≥about 60 min, ≥about 65 min, ≥about 70 min, ≥about 75 min, ≥about 80 min, ≥about 85 min, ≥about 90 min, ≥about 95 min, ≥about 100 min, ≥about 110 min or ≥about 120 min. Additionally or alternatively, the reheating interval may have a duration of ≤about 1 min, ≤about 5 min, ≤about 10 min, ≤about 15 min, ≤about 20 min, ≤about 25 min, ≤about 30 min, ≤about 35 min, ≤about 40 min, ≤about 45 min, ≤about 50 min, ≤about 55 min, ≤about 60 min, ≤about 65 min, ≤about 70 min, ≤about 75 min, ≤about 80 min, ≤about 85 min, ≤about 90 min, ≤about 95 min, ≤about 100 min, ≤about 110 min or ≤about 120 min. Ranges expressly disclosed include combinations of any of the above-enumerated values, e.g., about 1 to about 120 min, about 1 to about 90 min, about 4 to about 80 min, about 10 to about 75 min, etc. Preferably, the reaction interval may have a duration of about 1 to about 120 min, more preferably about 1 to about 90 min, more preferably about 1 to about 60 min, more preferably about 5 to about 40 min. Preferably, the duration of the reheating interval is less than the duration of the reaction interval; more preferably, the duration of the reheating interval is less than one half the duration of the reaction interval.

In various aspects, the reheating gas is provided by a suitable reheating apparatus, such as, but not limited to a fire heater. In the reheating apparatus, the reheating gas may be heated to a suitable temperature as described above prior to providing the reheating gas to a reaction zone. Additionally or alternatively, the reheating gas exiting a reaction zone may also be returned to the reheating apparatus to be reheated to a suitable temperature as described above and then provided to a reaction zone. The reheating apparatus may also make steam and/or heat the feedstock prior to the feedstock entering a reaction zone.

Additionally or alternatively, rejuvenated catalyst material may be separated from the reheating gas and/or volatile hydrocarbon in one or multiple separation steps inside or outside the reheating zone by any suitable means, such as, but not limited to cyclones. Additionally, the hydrogen gas may be used in the separation step.

C. Regeneration Interval

The process may further comprise a regeneration interval to recapture catalyst activity lost due to the accumulation of coke material and/or agglomeration of metal on the catalyst material during the reaction. This regeneration interval may be carried out when there has not been sufficient removal of the coke material from the particulate material (e.g., spent catalyst material) during the reheating intervals. For example, catalyst activity in a reaction zone may be restored to above about 50% of the fresh catalyst activity, preferably above about 80% of the fresh catalyst activity, and most preferably above about 95% and below about 99.9% of the fresh catalyst activity.

During the regeneration interval, the feedstock may be cyclically halted to a reaction zone. After halting the feedstock, purging of any combustible gas to below an explosive limit may be performed. For example, feedstock and/or reactor product (e.g., cyclopentadiene) may be purged to below an explosive limit. As used herein, the term "below an explosive limit" means that sufficient purging of any combustible gas has occurred such that when the gas flow is changed to a next composition (e.g., a regeneration gas), a hazardous mixture is not formed, which could result in an explosion. For example, if a combustible gas were present in the reaction zone and it is desired to introduce an oxidant, the system must first be purged with an inert to reduce combustible gas concentration such that the introduction of the oxidant-containing gas cannot create an explosive mixture.

A regeneration gas may then be supplied to the reaction zone, where the particulate material is contacted with the regeneration gas under regenerating conditions to oxidatively remove at least a portion of cumulatively deposited coke material on the catalyst material thereby forming a regenerated catalyst material. Suitable regeneration gases include, but are not limited to oxygen. The regeneration gas may flow in a direction counter-current or co-current to a direction of flow of the feedstock as described above for the reheating gas. The regeneration gas may further comprise an inert substance (e.g., $N_2$) as well. Following contacting with the regeneration gas in a reaction zone, purging of the regeneration gas to below an explosive limit may be performed. Once purging of the regeneration gas is complete, feedstock may then be provided to the reaction zone.

Preferably, the regeneration interval may have a duration of ≥about 0.5 day, ≥about 1 day, ≥about 1.5 days, ≥about 2 days, ≥about 3 days, ≥about 4 days, ≥about 5 days, ≥about 6 days, ≥about 7 days, ≥about 8 days, ≥about 9 days, ≥about 10 days, ≥about 11 days, ≥about 12 days, ≥about 13 days, ≥about 14 days, or ≥about 15 days. As used herein, the term "day" refers to an about 24 hour period, and the term "0.5 day" refers to an about 12 hour period. Additionally or alternatively, the regeneration interval may have a duration of ≤about 0.5 day, ≤about 1 day, ≤about 1.5 days, ≤about 2 days, ≤about 3 days, ≤about 4 days, ≤about 5 days, ≤about 6 days, ≤about 7 days, ≤about 8 days, ≤about 9 days, ≤about 10 days, ≤about 11 days, ≤about 12 days, ≤about 13 days, ≤about 14 days, or ≤about 15 days. Ranges expressly disclosed include combinations of any of the above-enumerated values, e.g., about 0.5 to about 15 days, about 1 to about 12 days, about 2 to about 11 days, etc. Preferably, the regeneration interval may have a duration of about 1 to about 15 days, more preferably about 1 to about 10 days, more preferably about 1.5 to about 5 days.

In various aspects, the regeneration interval may be performed at a frequency of about every 1 day, about every 2 days, about every 4 days, about every 6 days, about every 8 days, about every 10 days, about every 12 days, about every 14 days, about every 16 days, about every 18 days, about every 20 days, about every 22 days, about every 24 days, about every 26 days, about every 28 days, about every 30 days, about every 35 days, about every 40 days, about every 45 days, or about every 50 days. Ranges expressly disclosed include combinations of any of the above-enumerated values, e.g., about 1 to about 50 days, about 1 to about 45 days, about 2 to about 35 days, etc. Preferably, the regeneration interval may be performed at a frequency of every 1 to 50 days, more preferably every 10 to 45 days, more preferably every 20 to 40 days, more preferably every 30 to 35 days. Preferably, the regeneration interval may be performed at a frequency of 1 to 50 days, more preferably 10 to 45 days, more preferably 20 to 40 days, more preferably 30 to 35 days.

Additionally or alternatively, the reactor system may further comprise additional reaction zones, which may be operated in parallel, where the reaction zones alternate operating in a reaction interval, a reheating interval, and/or a regeneration interval. For example, the reactor system may comprise a first reaction zone, a second reaction zone, a third reaction zone, a fourth reaction zone, a fifth reaction zone, a sixth reaction zone, a seventh reaction zone, and/or an eighth reaction zone, etc. Preferably, the reactor system includes 1 to 20 reaction zones, more preferably 3 to 15 reaction zones, more preferably 5 to 10 reaction zones. Each reaction zone independently may be a fixed bed reactor or a fluidized bed reactor as described above. One cyclic arrangement of various reaction zones is shown in FIG. 1, where a first, second, third, and fourth reaction zone alternate between reaction intervals and reheating intervals, while a fifth reaction zone undergoes a regeneration interval.

In particular, the process described herein may further comprise a second reaction zone, and a third reaction zone operated in parallel with a first reaction zone. During the reaction interval in the first reaction zone, a reheating interval may be performed in the second reaction zone, wherein a second feedstock comprising acyclic $C_5$ hydrocarbons fed to the second reaction zone may be cyclically halted; a second reheating gas may be supplied to the second reaction zone and contacts a particulate material comprising a catalyst material to reheat the particulate material, and/or to remove at least a portion of incrementally deposited coke material on the catalyst material thereby forming a reheated particulate material and/or a rejuvenated catalyst material and a volatile hydrocarbon. Additionally, a regeneration interval may be performed in the third reaction zone, wherein a third feedstock comprising acyclic $C_5$ hydrocarbons fed to the third reaction zone may be cyclically halted; a regeneration gas may be supplied to the third reaction zone and contact a particulate material comprising a catalyst material under regenerating conditions to remove at least a portion of coke material deposited on the catalyst material thereby forming a regenerated catalyst material. Optionally, a reaction interval in the second reaction zone and a reaction interval in the third reaction zone may be performed, wherein the reaction interval in the first reaction zone, the reaction interval in the second reaction zone, and the reaction interval in the third reaction zone may be performed in a staggered fashion (i.e., be performed at different times).

Figure 2:
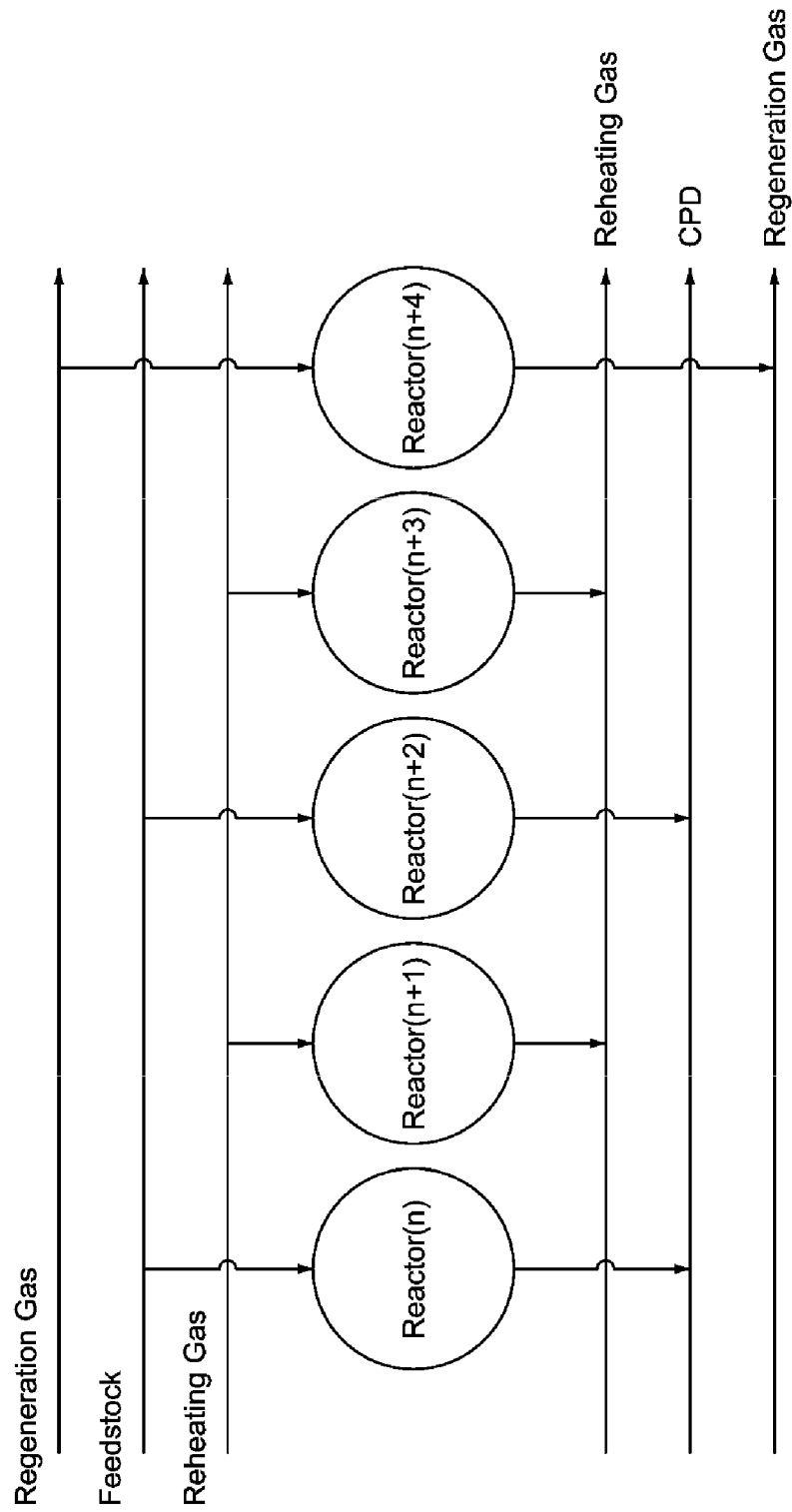
FIG. 2 shows an arrangement of reaction zones according to another embodiment of the invention.

Additionally, FIG. 2 shows another possible arrangement 220 for multiple reactors interconnected in parallel. Feedstock comprising $C_5$ hydrocarbons (e.g., acyclic $C_5$ hydrocarbons) may be distributed to all the reactors from one feedstock header 201 (not all conduits from every header to every reactor are shown in FIG. 2). Product may be collected from all the reactors via one product header 204. Similarly, there may be one reheating gas supply header 202 for the reheating gas and/or one regeneration gas supply header 200 for regeneration gas that is distributed to all the reactors. A regeneration effluent gas header 203 may collect regeneration gas effluent from all the reactors. Likewise, a reheating gas effluent header 205 may collect reheating gas effluent from all the reactors. While an arrangement of five (5) reactors is shown in FIG. 2, the invention is not limited by this number. Arrangements of multiple reactors having 2, 3, 4, 5, 6, 7, 8, 9, 10, or more reactors are suitable for the invention. Preferable is a multiple reactor arrangement having 5 reactors.

Feedstock comprising acyclic $C_5$ may be provided from feedstock header 201 to at least one reactor, e.g., via conduit 206 to reactor 211 and/or via conduit 208 to reactor 213, as part of a reaction cycle or an "on-oil" conversion cycle. Reactor effluent comprising cyclic $C_5$ product exiting the "on-oil" reactors (e.g., via conduits 216 and/or 218) may be combined and conducted away via common product header 204. Concurrent to the "on-oil" conversion, reheating gas may be provided to one or more reactors, e.g., via conduit 207 to reactor 212 and/or via conduit 209 to reactor 214. Similarly, regeneration gas and purge gas may be provided concurrently to one or more reactors through regeneration gas supply header 200, e.g., via conduit 210 to reactor 215. Regeneration gas effluent may be collected from the one or more reactors, which were provided regeneration gas and purge gas. For example, regeneration gas effluent may be collected from reactor 215 via conduit 220 to regeneration gas effluent header 203. Reheating gas effluent may be collected from the one or more reactors, which were provided reheating gas. For example, reheating gas effluent may be collected from reactor 212 via conduit 217 and/or reactor 214 via conduit 219 to reheating gas effluent header 205. Each reactor is designed with valving systems not shown to enable isolation from various headers when not in use between on-oil feedstock conversion, reheat, and/or regeneration cycles. Any valving system and control system known in the art may be used; e.g., double block and bleed to prevent contacting of flammable gases and oxidant gases.

Advantageously, the conversion process can comprise a cyclic arrangement for concurrent "on-oil" feedstock conversion, reheating, and/or regeneration in a multiple reactor conversion system. "On-oil" conversion time is typically greater than 1 minute, typically greater than 5 minutes, often from about 1 minute to about 120 minutes. Reheating time is typically from about 1 minute to about 120 minutes. The arrangement 220 in FIG. 2 allows for multiple reactors, e.g., reactors 211, 212, 213, and 215, to repeat a rotating cycle of "on-oil" conversion and reheating, while at least one other reactor, e.g., reactor 215, completes regeneration. When regeneration of a reactor, e.g., reactor 215, is complete, it may be returned to "on-oil" conversion/reheat cycle while another reactor, e.g., reactor 211, may be cycled out for regeneration as required. Advantageously, such an arrangement provides more consistent product composition while reducing the amount of equipment needed.

III. Reaction Systems for Conversion of Acyclic $C_5$

Figure 3:
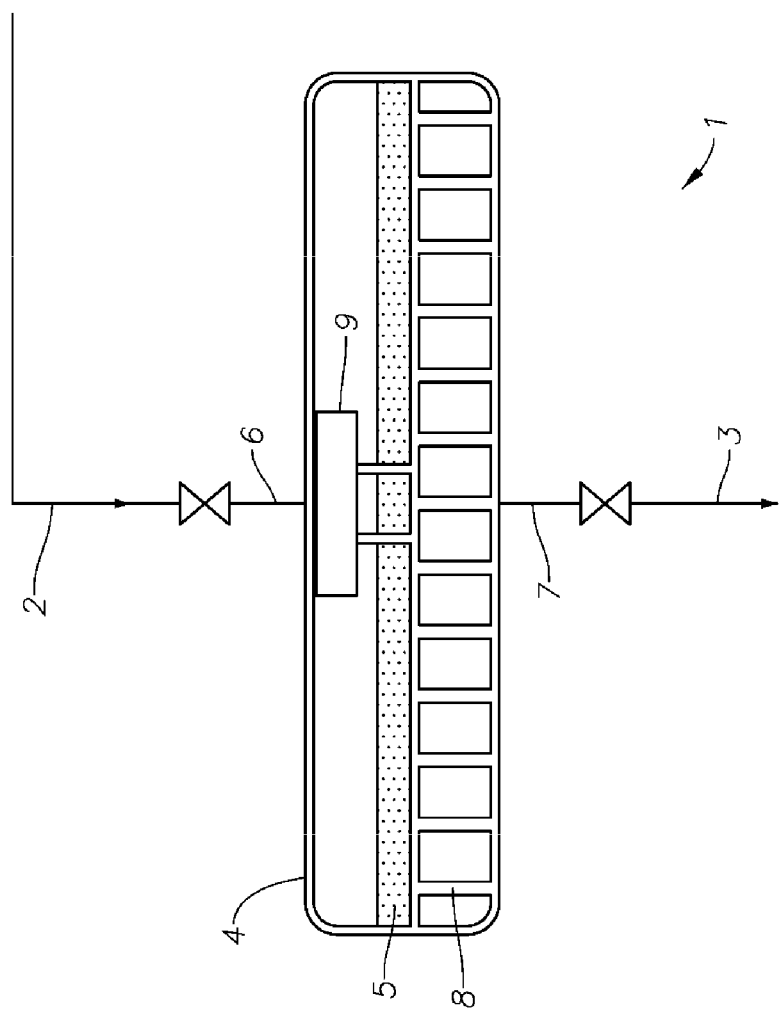
FIG. 3 is a diagram of a reactor according to another embodiment of the invention.

In another embodiment, a reaction system 1 for converting $C_5$ hydrocarbons (e.g., acyclic $C_5$ hydrocarbons) to cyclopentadiene is provided, as shown in FIG. 3. The reaction system 1 may comprise a feedstock stream 2 comprising $C_5$ hydrocarbons (e.g., acyclic Cs hydrocarbons) as described above, an effluent stream 3 comprising cyclopentadiene; and at least one reactor 4 as described above. The at least one reactor 4 may comprise a particulate material 5 comprising a catalyst material as described above, a feedstock inlet 6 for providing the feedstock stream 2 to the reaction system 1, and an effluent outlet 7 for removal of the first effluent stream 3.

The at least one reactor 4 may be a fixed bed reactor (e.g., horizontal or vertical fixed bed reactor) or a fluidized bed reactor as described above. Preferably, the at least one reactor 4 may include at least one internal structure (not shown) as described above. For example, the at least one reactor 4 may include a support 8 for the particulate material and/or a distributer 9.

The at least one reactor 4 is operated under reaction conditions as described above to convert at least a portion of the $C_5$ hydrocarbons (e.g., acyclic $C_5$ hydrocarbons) to cyclopentadiene. Additionally, it is preferable that the at least one reactor 4 has an inverse temperature profile as described above. In particular, the feedstock stream 2 at the feedstock inlet may have a temperature of less than about 525° C. and/or the effluent stream 3 at the effluent outlet has a temperature of at least about 575° C. Additionally, the reaction conditions may comprise a temperature of about 400° C. to about 700° C. and/or a pressure of about 3 psia to about 30 psia. Preferably, at least about 30 wt % of the acyclic $C_5$ hydrocarbons is converted to cyclopentadiene. Optionally, the at least one reactor 4 may include one or more heating devices (e.g., fired tube, heated coil) (not shown) in order to maintain temperature therein.

Particularly, the particulate material comprises less than about 25.0 wt % catalyst material as described above and further comprises an inert material as described above (e.g., at least about 25.0 wt %). The catalyst material and/or the inert material may have an average diameter as described above, e.g., about 1.0 mm to about 20 mm and about 3.0 mm to about 20 mm, respectively. Preferably, the catalyst material comprises platinum on ZSM-5, platinum on zeolite L, and/or platinum on silica, preferably platinum on ZSM-5. Additionally, the particulate material may provide at least a portion of (e.g., at least about 50%) the heat required for converting the $C_5$ hydrocarbons (e.g., acyclic $C_5$ hydrocarbons) to cyclopentadiene.

Additionally, the reaction system 1 may further comprise a cyclone (not shown) for separating the particulate material, which may be entrained with hydrocarbons (e.g. cyclopentadiene) in the effluent stream 3. Another effluent stream (not shown) substantially free of particulate material may then travel to a product recovery system.

Figure 4:
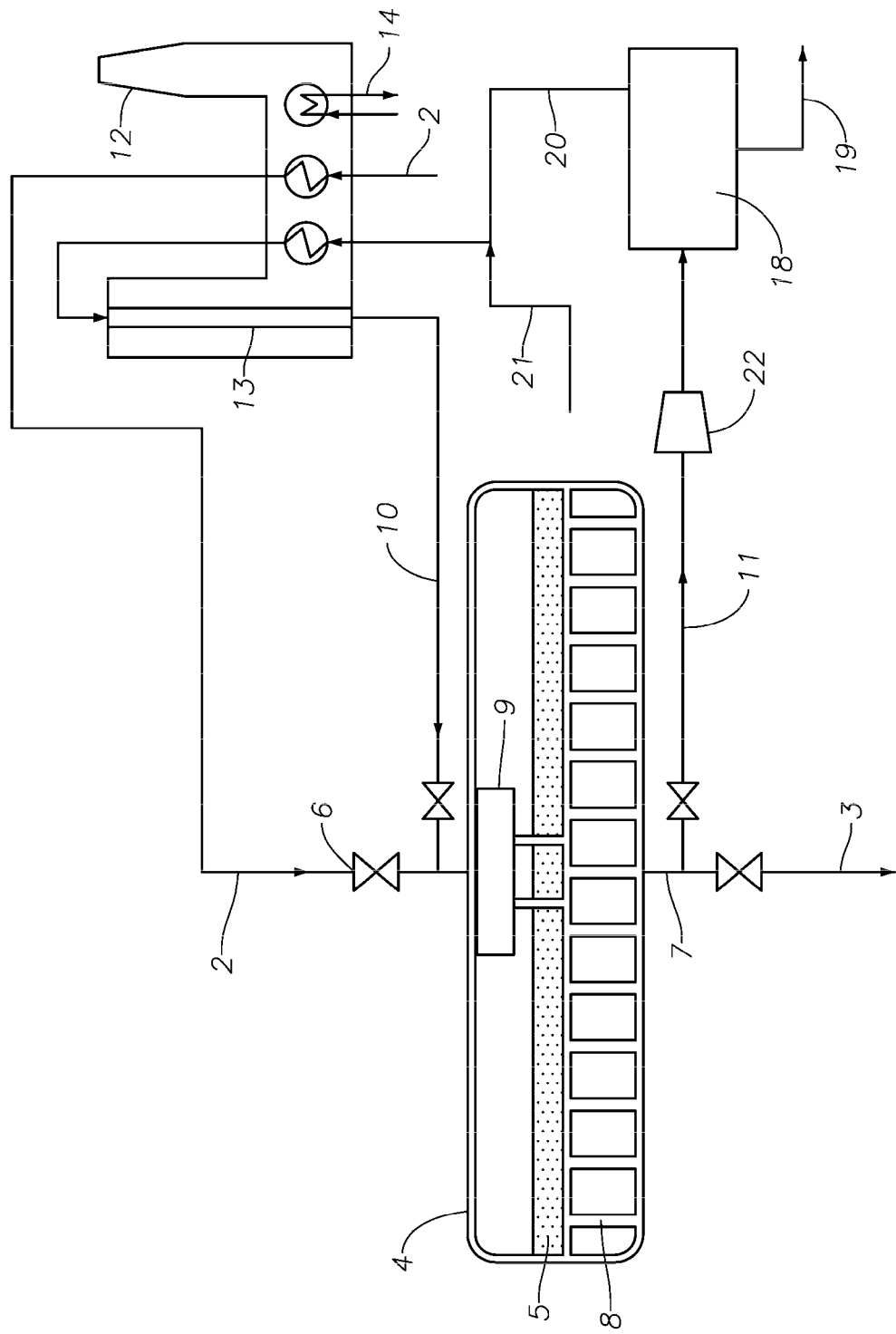
FIG. 4 is a diagram of a reactor with a reheating apparatus according to another embodiment of the invention.

In another embodiment, the reaction system 1 may further comprise a reheating gas stream 10 for reheating the particulate material and/or restoring activity of the spent catalyst material, as shown in FIG. 4. The reheating gas stream 10 may enter via feedstock inlet 6 or via a different inlet (not shown). The reheating gas stream 10 may comprise an inert substance (e.g., CO, $N_2$) and/or hydrogen for removal of at least a portion of incrementally deposited coke material on spent catalyst material thereby forming a rejuvenated catalyst material, and a volatile hydrocarbon. Further, the rejuvenated catalyst material comprises less of the incrementally deposited coke material than the spent catalyst material as described above, preferably at least about 10 wt % less of the incrementally deposited coke material than the spent catalyst material. After a suitable duration as described above, the reheating gas and, optionally, the volatile hydrocarbon, may exit the at least one reactor 4 via the effluent outlet 7 or a different outlet (not shown) as an effluent reheating gas stream 11. In particular, the reheating gas stream 10 has an inlet temperature and pressure as described above, preferably an inlet temperature of at least about 600° C. and/or an inlet pressure of about 100 psia. Further, the rejuvenated catalyst material comprises less of the incrementally deposited coke material than the spent catalyst material as described above, preferably at least about 10 wt % less of the incrementally deposited coke material than the spent catalyst material. The reheating gas stream 10 may flow in a co-current or counter-current direction to a direction of flow of the feedstock stream 2, preferably in counter-current direction. Further, the reheating gas stream 10 may be provided by a reheating apparatus 12 as described above in fluid connection with the at least one reactor 4. The effluent reheating gas stream 11 may be sent to a compression device 22 and then sent to a separation apparatus 18 wherein a light hydrocarbon enriched gas stream 19 and a light hydrocarbon depleted gas stream 20 may be produced. The light hydrocarbon enriched gas stream 19 may be used, inter alia, as a fuel. The light hydrocarbon depleted gas stream 20 may be combined with a make-up hydrogen stream 21 and heated in reheating apparatus 12. The reheating apparatus 12 may comprise one or more heating devices as described above, a reheating inlet for the light hydrocarbon depleted gas stream 20, a means 13 for heating the light hydrocarbon depleted gas stream 20 to produce the reheating gas stream 10, and a reheating outlet (not shown) for returning the reheating gas stream 10 to the at least one reactor 4. The means 13 for heating the recycled reheating gas stream 11 may include any suitable means known in the art, for example, a fired heater as described above. The separation apparatus 18 may be a membrane system, adsorption system, or other known system for separation of $H_2$ from light hydrocarbons.

In particular, the reheating apparatus 12 operates under conditions described above, preferably reheating apparatus 12 has a temperature of about 550° C. to about 800° C. Additionally, the reheating apparatus 12 may produce a steam stream 14, typically from water, but steam is also possible. Also, the reheating apparatus 12 may heat feedstock stream 2 prior to feedstock stream 2 entering the at least one reactor 4.

Figure 5:
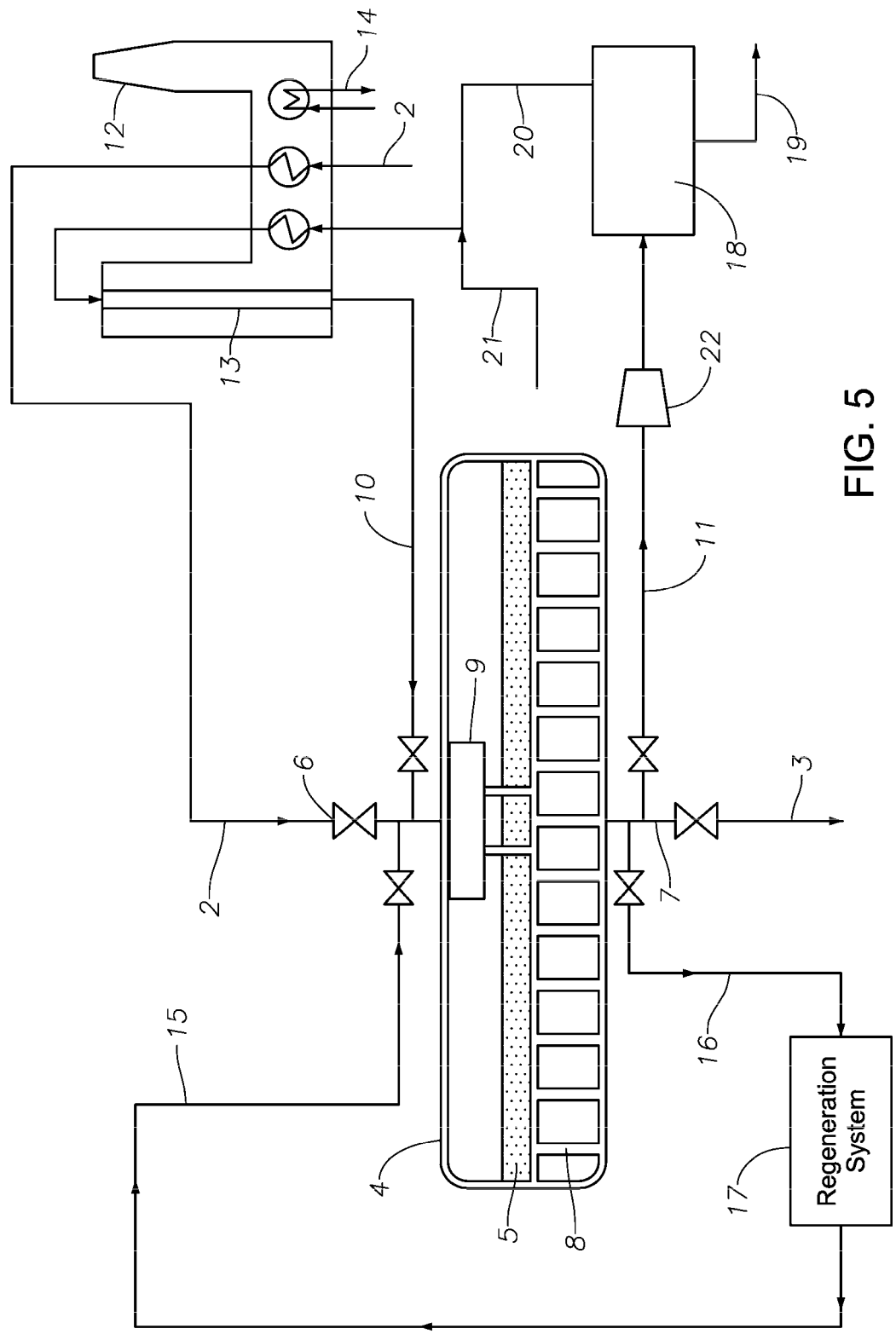
FIG. 5 is a diagram of a reactor with a reheating apparatus and a regenerating apparatus according to another embodiment of the invention.

In another embodiment, the reaction system 1 may further comprise a regeneration gas stream 15, as shown in FIG. 5. The regeneration gas stream 15 may enter via feedstock inlet 6 or via a different inlet (not shown), under regeneration conditions as described above for removing at least a portion of coke material deposited on the catalyst material (e.g., spent catalyst material) thereby forming a regenerated catalyst material. After suitable duration as described above, the regeneration gas may exit the at least one reactor 4 via the effluent outlet 7 or a different outlet (not shown) as a recycled regeneration gas stream 16. The regeneration gas stream 15 may be provided by a regeneration apparatus 17 as described above in fluid connection with the at least one reactor 4.

Additionally or alternatively, the reaction system 1 may further comprise a fresh particulate material stream (not shown) in fluid connection with the at least one reactor 6.

Additionally or alternatively, the at least one reactor 4 may comprise at least a first reactor, a second reactor, a third reactor, a fourth reactor, a fifth reactor, a sixth reactor, a seventh reactor, an eighth reactor, etc. Preferably, the reaction system includes 1 to 20 reactors, more preferably 3 to 15 reactors, more preferably 5 to 10 reactors. Where the at least one reactor 4 includes a first, a second, and a third reactor, the reactors may be operated in parallel, wherein the first reactor, the second reactor, and third reactor independently, cyclically operate under a reaction interval, a rejuvenation interval, and/or a regeneration interval. Each reactor independently may be a fixed bed or a fluidized bed reactor.

IV. Further Embodiments

This invention further relates to:

Embodiment 1. A process for converting acyclic $C_5$ hydrocarbons to cyclopentadiene in a reactor system, wherein the process comprises: a reaction interval comprising: cyclically providing to the reactor system a feedstock comprising acyclic $C_5$ hydrocarbons; contacting the feedstock with a particulate material comprising a catalyst material (e.g., platinum on ZSM-5, platinum on zeolite L, and/or platinum on silica) in a first reaction zone (e.g., fixed bed reactor, fluidized bed reactor, horizontal fixed bed reactor, vertical fixed bed reactor) under reaction conditions to convert at least a portion of the acyclic $C_5$ hydrocarbons to a first effluent comprising cyclopentadiene; and a reheating interval comprising: cyclically halting the feedstock to the first reaction zone; and providing a reheating gas to the first reaction zone to reheat the particulate material.

Embodiment 2. The process of embodiment 1, wherein an inverse temperature profile is maintained in the first reaction zone.

Embodiment 3. The process of embodiment 1 or 2, wherein the feedstock flows co-current or counter-current to a direction of a flow of the reheating gas.

Embodiment 4. The process of any one of the previous embodiments, wherein the feedstock is provided at a temperature of less than or equal to about 525° C. and/or the first effluent exiting the first reaction zone has a temperature of at least about 575° C.

Embodiment 5. The process of any one of the previous embodiments, wherein the reaction interval has a duration of about 1 min to about 90 min and/or the reaction interval is performed until the temperature in the first reaction zone falls below about 450° C. to about 550° C.

Embodiment 6. The process of any one of the previous embodiments, wherein the reheating gas comprises hydrogen and the reheating gas contacts the particulate material to remove at least a portion of incrementally deposited coke material (e.g., at least about 10.0 wt %) on the catalyst material thereby forming a rejuvenated catalyst material and volatile hydrocarbon and/or the reheating gas flows co-current or counter-current to a direction of flow of the feedstock.

Embodiment 7. The process of any one of the previous embodiments, wherein the reheating gas enters the first reaction zone at a temperature of at least about 600° C. and a pressure of about 100 psia.

Embodiment 8. The process of any one of the previous embodiments, wherein the reheating interval has a duration of about 1 min to about 90 min.

Embodiment 9. The process of any one of the previous embodiments, wherein the reaction conditions comprise a temperature of about 400° C. to about 700° C. and an outlet pressure of about 3 psia to about 30 psia and/or at least about 30 wt % of the acyclic $C_5$ hydrocarbons is converted to cyclopentadiene.

Embodiment 10. The process of any one of the previous embodiments, wherein the particulate material further comprises an inert material (e.g., at least about 25.0 wt %) and/or at less than about 25.0 wt % catalyst material.

Embodiment 11. The process of any one of the previous embodiments, wherein the catalyst material has an average diameter of about 1.0 mm to about 20.0 mm μm and/or the inert material has an average diameter of about 3.0 mm to about 20.0 mm.

Embodiment 12. The process of any one of the previous embodiments, wherein the particulate material provides at least about 50% of heat required for converting at least a portion of the acyclic $C_5$ hydrocarbons to the first effluent comprising cyclopentadiene.

Embodiment 13. The process of any one of the previous embodiments, wherein the first reaction zone comprises at least one heating device.

Embodiment 14. The process of any one of the previous embodiments further comprising cyclically halting the feedstock to the first reaction zone; supplying a regeneration gas to the first reaction zone; and contacting the particulate material with the regeneration gas under regenerating conditions to remove at least a portion of coke material deposited on the catalyst material thereby forming a regenerated catalyst material.

Embodiment 15. The process of embodiment 14, wherein the regeneration interval occurs at an interval of every about 1 day to about 30 days.

Embodiment 16. The process of any one of the previous embodiments further comprising a second reaction zone (e.g., fixed bed reactor or fluidized bed reactor), and a third reaction zone (e.g., fixed bed reactor or fluidized bed reactor) operated in parallel with the first reaction zone; wherein during the reaction interval in the first reaction zone: a reheating interval is performed in the second reaction zone, wherein a second feedstock comprising acyclic $C_5$ hydrocarbons fed to the second reaction zone is cyclically halted; a second reheating gas is supplied to the second reaction zone and contacts a particulate material comprising a catalyst material to reheat the particulate material and/or remove at least a portion of incrementally deposited coke material on the catalyst material thereby forming a reheated and/or rejuvenated catalyst material and a volatile hydrocarbon; and a regeneration interval is performed in the third reaction zone, wherein a third feedstock comprising acyclic $C_5$ hydrocarbons fed to the third reaction zone is cyclically halted; a regeneration gas is supplied to the third reaction zone and contacts a particulate material comprising a catalyst material under regenerating conditions to remove at least a portion of coke material deposited on the catalyst material thereby forming a regenerated catalyst material, optionally further comprising performing a reaction interval in the second reaction zone and a reaction interval in the third reaction zone, wherein the reaction interval in the first reaction zone, the reaction interval in the second reaction zone, and the reaction interval in the third reaction zone are performed in a staggered fashion.

Embodiment 17. The process of any one of the previous embodiments further comprising providing fresh particulate material to the first reaction zone.

Embodiment 18. A reaction system for converting acyclic $C_5$ hydrocarbons to cyclopentadiene, wherein the reaction system comprises: a feedstock stream comprising acyclic $C_5$ hydrocarbons; a first effluent stream comprising cyclopentadiene; a reheating gas stream and at least one reactor (e.g., fixed bed reactor, fluidized bed reactor, horizontal fixed bed reactor, vertical fixed bed reactor) operated under reaction conditions to convert at least a portion of the acyclic $C_5$ hydrocarbons to cyclopentadiene; wherein the at least one reactor comprises: a particulate material comprising a catalyst material (e.g., platinum on ZSM-5, platinum on zeolite L, and/or platinum on silica); a feedstock inlet for providing the feedstock stream and/or the reheating gas stream to the reaction system; and an effluent outlet for removal of the first effluent stream and/or the reheating gas stream.

Embodiment 19. The reaction system of embodiment 18, wherein the at least one reactor has an inverse temperature profile and/or the feedstock stream has a flow in a co-current or a counter-current direction to a flow of the reheating gas stream.

Embodiment 20. The reaction system of embodiment 18 or 19, wherein the feedstock stream at the feedstock inlet has a temperature of less than about 525° C. and/or the first effluent stream at the effluent outlet has a temperature of at least about 575° C.

Embodiment 21. The reaction system of any one of embodiments 18, 19, or 20, wherein the at least one reactor further comprises at least one heating device.

Embodiment 22. The reaction system of any one of embodiments 18, 19, 20, or 21, wherein the reaction conditions comprise a temperature of about 400° C. to about 700° C. and a pressure of about 3 psia to about 30 psia and/or at least about 30 wt % of the acyclic $C_5$ hydrocarbons is converted to cyclopentadiene.

Embodiment 23. The reaction system of any one of embodiments 18, 19, 20, 21, or 22, wherein the particulate material further comprises an inert material (at least about 25.0 wt %) and/or less than about 25.0 wt % catalyst material.

Embodiment 24. The reaction system of any one of embodiments 18, 19, 20, 21, 22, or 23, wherein the catalyst material has an average diameter of about 1.0 mm to about 20.0 mm μm and/or the inert material has an average diameter of about 3.0 mm to about 20.0 mm.

Embodiment 25. The reaction system of any one of embodiments 18, 19, 20, 21, 22, 23, or 24, wherein the particulate material provides at least about 50% of heat required for converting at least a portion of the acyclic $C_5$ hydrocarbons to the first effluent comprising cyclopentadiene.

Embodiment 26. The reaction system of any one of embodiments 18, 19, 20, 21, 22, 23, 24, or 25, wherein the reheating gas stream comprises hydrogen for removal of at least a portion of incrementally deposited coke material on spent catalyst material thereby forming a rejuvenated catalyst material and a volatile hydrocarbon.

Embodiment 27. The reaction system of embodiment 26, wherein the reheating gas stream has an inlet temperature of at least about 600° C. and an inlet pressure of about 100 psia and/or the rejuvenated catalyst material comprises at least about 10 wt % less of the incrementally deposited coke material than the spent catalyst material.

Embodiment 28. The reaction system of any one of embodiments 18, 19, 20, 21, 22, 23, 24, 25, 26, or 27 further comprising a regeneration gas stream, wherein the inlet provides the regeneration gas stream to the at least one reactor under regenerating conditions to remove at least a portion of coke material deposited on the catalyst material thereby forming a regenerated catalyst material.

Embodiment 29. The reaction system of any one of embodiments 18, 19, 20, 21, 22, 23, 24, 25, 26, 27, or 28 further comprising a fresh particulate material stream in fluid connection with the at least one reactor.

Embodiment 30. The reaction system of any one of embodiments 18, 19, 20, 21, 22, 23, 24, 25, 26, 27, 28, or 29, wherein the at least one reactor comprises at least a first reactor (e.g., fixed bed reactor, fluidized bed reactor), a second reactor (e.g., fixed bed reactor, fluidized bed reactor) and a third reactor (e.g., fixed bed reactor, fluidized bed reactor) operated in parallel, wherein the first reactor, the second reactor, and third reactor, independently, cyclically operate under a reaction interval, a rejuvenation interval, and/or a regeneration interval.

This invention further relates to the following embodiments 31 to 52:

Embodiment 31. A reaction system for converting acyclic $C_5$ hydrocarbons to cyclopentadiene, wherein the reaction system comprises:
a feedstock stream comprising acyclic $C_5$ hydrocarbons;
a first effluent stream comprising cyclopentadiene;
a reheating gas stream; and
at least one reactor operated under reaction conditions to convert at least a portion of the acyclic $C_5$ hydrocarbons to cyclopentadiene; wherein the at least one reactor comprises:

a particulate material comprising a catalyst material;
a feedstock inlet for providing the feedstock stream and/or the reheating gas stream to the reaction system; and
an effluent outlet for removal of the first effluent stream and/or the reheating gas stream.

Embodiment 32. The reaction system of embodiment 31, wherein the at least one reactor has an inverse temperature profile.

Embodiment 33. The reaction system of embodiment 31, wherein the at least one reactor is a fixed bed reactor or a fluidized bed reactor.

Embodiment 34. The reaction system of embodiment 31, wherein at least one reactor is a horizontal fixed bed reactor or a vertical fixed bed reactor.

Embodiment 35. The reaction system of embodiment 31, wherein the feedstock stream has a flow in a co-current direction or a counter-current direction to a flow of the reheating gas stream.

Embodiment 36. The reaction system of embodiment 31, wherein the feedstock stream at the feedstock inlet has a temperature of less than about 525° C.

Embodiment 37. The reaction system of embodiment 31, wherein the first effluent stream at the effluent outlet has a temperature of at least about 575° C.

Embodiment 38. The reaction system of embodiment 31, wherein the reheating gas stream comprises hydrogen for removal of the at least a portion of incrementally deposited coke material on spent catalyst material thereby forming a rejuvenated catalyst material and a volatile hydrocarbon.

Embodiment 39. The reaction system of embodiment 31, wherein the reheating gas stream has an inlet temperature of at least about 600° C. and an inlet pressure of about 100 psia.

Embodiment 40. The reaction system of embodiment 38, wherein the rejuvenated catalyst material comprises at least about 10 wt % less of the incrementally deposited coke material than the spent catalyst material.

Embodiment 41. The reaction system of embodiment 31 further comprising:
a regeneration gas stream, wherein the feedstock inlet provides the regeneration gas stream to the at least one reactor under regenerating conditions to remove at least a portion of coke material deposited on the catalyst material thereby forming a regenerated catalyst material.

Embodiment 42. The reaction system of embodiment 31, wherein the at least one reactor further comprises at least one heating device.

Embodiment 43. The reaction system of embodiment 31, wherein the reaction conditions comprise a temperature of about 400° C. to about 700° C. and an outlet pressure of about 3 psia to about 30 psia.

Embodiment 44. The reaction system of embodiment 31, wherein at least about 30 wt % of the acyclic $C_5$ hydrocarbons is converted to cyclopentadiene.

Embodiment 45. The reaction system of embodiment 31, wherein the particulate material further comprises an inert material.

Embodiment 46. The reaction system of embodiment 45, wherein the catalyst material has an average diameter of about 1.0 mm to about 20.0 mm and the inert material has an average diameter of about 3.0 mm to about 20.0 mm.

Embodiment 47. The reaction system of embodiment 45, wherein the particulate material comprises at least about 25 wt % inert material.

Embodiment 48. The reaction system of embodiment 31, wherein the particulate material comprises less than about 25 wt % catalyst material.

Embodiment 49. The reaction system of embodiment 31, wherein the catalyst material comprises platinum on ZSM-5.

Embodiment 50. The reaction system of embodiment 31, wherein the particulate material provides a portion of (such as, at least about 50%) of heat required for converting the acyclic $C_5$ hydrocarbons to cyclopentadiene.

Embodiment 51. The reaction system of embodiment 31, wherein the at least one reactor comprises at least a first reactor, a second reactor, and a third reactor operated in parallel, wherein the first reactor, the second reactor, and third reactor, independently, and cyclically operate under a reaction interval, a rejuvenation interval, and/or a regeneration interval.

Embodiment 52. The reaction system of embodiment 50, wherein the first reactor, the second reactor, and third reactor are each, independently, a fixed bed reactor or a fluidized bed reactor.

Embodiment 53. The reaction system of embodiment 51 further comprising a fresh particulate material stream in fluid connection with the at least one reactor.

This invention further relates to the following embodiments 54 to 56:

Embodiment 54. A process for converting acyclic $C_5$ hydrocarbons to cyclopentadiene in a reactor system, wherein the process comprises:
a reaction interval comprising:
cyclically providing to the reactor system a feedstock comprising acyclic $C_5$ hydrocarbons;
contacting the feedstock with a particulate material comprising a catalyst material in a first reaction zone under reaction conditions to convert at least a portion of the acyclic $C_5$ hydrocarbons to a first effluent comprising cyclopentadiene; and a reheating interval comprising:
cyclically halting the feedstock to the first reaction zone; and
providing a reheating gas to the first reaction zone to reheat the particulate material,
further comprising a second reaction zone, and a third reaction zone operated in parallel with the first reaction zone;
wherein during the reaction interval in the first reaction zone:
a reheating interval is performed in the second reaction zone, wherein a second feedstock comprising acyclic $C_5$ hydrocarbons fed to the second reaction zone is cyclically halted; a second reheating gas is supplied to the second reaction zone and contacts a particulate material comprising a catalyst material to reheat the particulate material and/or remove at least a portion of incrementally deposited coke material on the catalyst material thereby forming a reheated and/or rejuvenated catalyst material and a volatile hydrocarbon; and
a regeneration interval is performed in the third reaction zone, wherein a third feedstock comprising acyclic $C_5$ hydrocarbons fed to the third reaction zone is cyclically halted; a regeneration gas is supplied to the third reaction zone and contacts a particulate material comprising a catalyst material under regenerating conditions to remove at least a portion of coke material deposited on the catalyst material thereby forming a regenerated catalyst material.

Embodiment 55. The process of embodiment 54 further comprising performing a reaction interval in the second reaction zone and a reaction interval in the third reaction zone, wherein the reaction interval in the first reaction zone, the reaction interval in the second reaction zone, and the reaction interval in the third reaction zone are performed in a staggered fashion.

Embodiment 56. The process of embodiment 54, wherein the first reaction zone, the second reaction zone, and the third reaction zone are each independently a fixed bed reactor or a fluidized bed reactor.

This invention further relates to a process for converting acyclic $C_5$ hydrocarbons to cyclopentadiene in a reactor system, wherein the process comprises:
  a reaction interval comprising:
    cyclically providing to the reactor system a feedstock comprising acyclic $C_5$ hydrocarbons;
    contacting the feedstock with a particulate material comprising a catalyst material in a first reaction zone under reaction conditions to convert at least a portion of the acyclic $C_5$ hydrocarbons to a first effluent comprising cyclopentadiene; and
  a reheating interval comprising:
    cyclically halting the feedstock to the first reaction zone; and
    providing a reheating gas to the first reaction zone to reheat the particulate material, wherein fresh particulate material is provided to the first reaction zone.

INDUSTRIAL APPLICABILITY

The first hydrocarbon reactor effluent obtained during the acyclic $C_5$ conversion process containing cyclic, branched and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

Scheme I

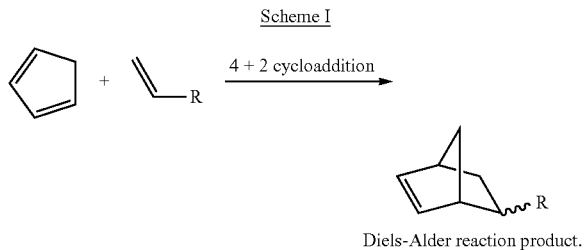

Diels-Alder reaction product.

where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono-olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins, and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

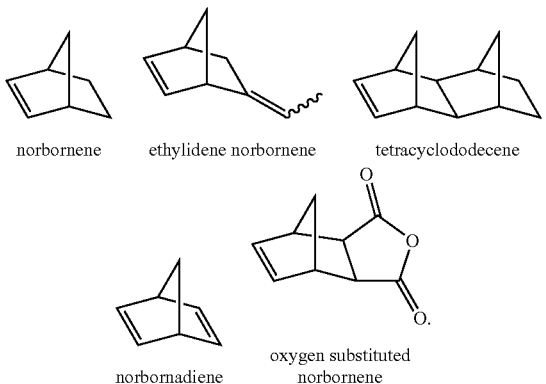

norbornene   ethylidene norbornene   tetracyclododecene norbornadiene   oxygen substituted norbornene The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

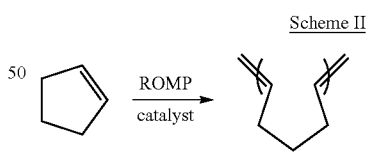

Separated cyclopentane is useful as a blowing agent and as a solvent. Linear and branched $C_5$ products are useful for conversion to higher olefins and alcohols. Cyclic and non-cyclic $C_5$ products, optionally after hydrogenation, are useful as octane enhancers and transportation fuel blend components.

EXAMPLES

Example 1

A mixture with ~22% solids was prepared by mixing 950 g of DI water, 53.5 g of 50% NaOH solution, 76.8 g of n-propyl amine 100% solution, 10 g of ZSM-5 seed crystals, and 336 g of Ultrasil PM™ Modified silica, and 4.4 g of Silver Nitrate in a 2-liter container. The mixture was then charged into a 2-liter autoclave. The mixture had the following molar composition:

$SiO_2/Al_2O_3 > 1000$
$H_2O/SiO_2 \sim 10.98$
$OH/SiO_2 \sim 0.17$
$Na/SiO_2 \sim 0.17$
$n\text{-}PA/Si \sim 0.25$.

In the autoclave, the mixture was mixed at 250 rpm and reacted at 230° F. (110° C.) for 72 hours. The resulting products were filtered and washed with deionized water then dried overnight at 250° F. (120° C.). The XRD pattern (not shown) of the as-synthesized material showed the typical pure phase of ZSM-5 topology. The SEM (not shown) of the as-synthesized material showed that the material was composed of a mixture of large crystals with a size of <1 micron. The resulting ZSM-5 crystals had a $SiO_2/Al_2O_3$ molar ratio of >800, Na of ~0.28%, and Ag of 0.9 wt %

This material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F., the oxygen content was increased to 16.8%, and the material was held at 1000° F. for 6 hours. After cooling, 0.45 wt % Pt was added via incipient wetness impregnation using an aqueous solution of tetraamine platinum hydroxide. The catalyst was then dried in air at room temperature at 250° F. (120° C.), and calcined in air for three hours at 660° F. (350° C.). The catalyst powder was pressed (15 ton), crushed, and sieved to obtain 40-60 mesh particle size.

Example 2

Figure 6:
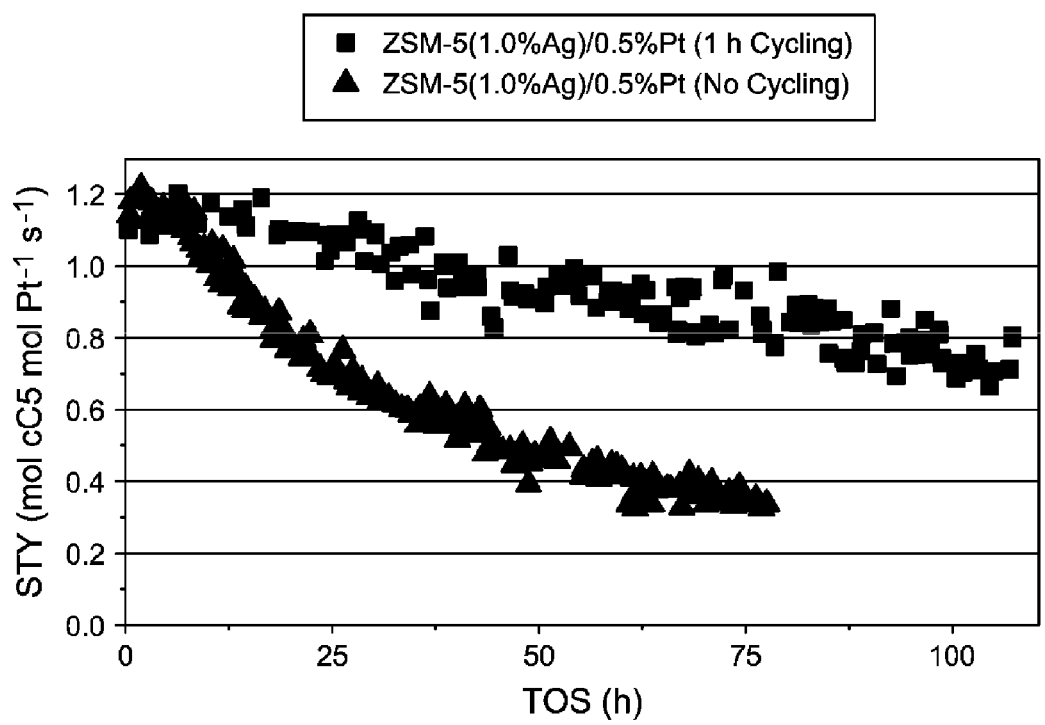
FIG. 6 illustrates the site-time-yield (STY) of cyclic $C_5$ hydrocarbons (i.e., the mols of cC5/mol of Pt/second) against T.O.S. in Example 2 under a continuously-on-oil reactor operating strategy and an intermittent H2 rejuvenation reactor operating strategy.

The catalyst of Example 1 was tested under two reactor operating strategies: a continuously on-oil strategy and an intermittent H2 rejuvenation strategy. The catalyst (0.5 g) was physically mixed with quartz (1.5 g, 60-80 mesh) and loaded into a ⅜" OD, 18" long stainless steel reactor. The catalyst bed was held in place with quartz wool and the reactor void space was loaded with coarse quartz particles. The catalyst was dried for 1 hour under He (100 mL/min, 30 psig, 250° C.) then reduced for 1 hour under H2 (200 mL/min, 30 psig, 500° C.). The catalyst was then tested for performance with a feed containing n-pentane, H2, and balance He. The test conditions for a continuously on-oil operating strategy were the following: 0.5 g [0.96% Ag]-ZSM-5/0.5% Pt, 5.0 psia C5H12, 1:1 molar H2:C5, 14.7 WHSV, 45 psia total during the on-oil period. The test conditions for an intermittent H2 rejuvenation strategy were the following: the reactor was cycled for one hour on-oil and one hour on H2 rejuvenation at the conditions of 200 cm3 min-1 H2 at 600° C. and 45 psia of all H2; i.e., with no additional He. Performance results for both operating strategies are shown in FIG. 6 as the site-time-yield of cyclic C5's (i.e., the mols of cC5/mol of Pt/second). FIG. 6 demonstrates that the H2 rejuvenation is capable of improving catalyst capability over time to catalyze $C_5$ hydrocarbon cyclization.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for converting acyclic $C_5$ hydrocarbons to cyclic $C_5$s including cyclopentadiene in a reactor system, wherein the process comprises:
   a reaction interval comprising:
   cyclically providing to the reactor system a feedstock comprising acyclic $C_5$ hydrocarbons;
   contacting the feedstock with a particulate material comprising a catalyst material in a first reaction zone under reaction conditions to convert at least a portion of the acyclic $C_5$ hydrocarbons to a first effluent comprising cyclopentadiene; and
   a reheating interval comprising:
   cyclically halting the feedstock to the first reaction zone; and
   providing a reheating gas to the first reaction zone to reheat the particulate material.

2. The process of claim 1, wherein an inverse temperature profile or an isothermal temperature profile is maintained in the first reaction zone.

3. The process of claim 1, wherein the first reaction zone is a fixed bed reactor or a fluidized bed reactor.

4. The process of claim 1, wherein the first reaction zone is a horizontal fixed bed reactor or a vertical fixed bed reactor.

5. The process of claim 1, wherein the feedstock flows co-current or counter-current to a direction of a flow of the reheating gas.

6. The process of claim 1, wherein the feedstock is provided at a temperature of less than or equal to about 525° C.

7. The process of claim 1, wherein the first effluent exiting the at least first reaction zone has a temperature of at least about 575° C.

8. The process of claim 1, wherein the reaction interval is performed until the temperature in the first reaction zone falls below about 550° C.

9. The process of claim 1, wherein the reheating gas comprises hydrogen and the reheating gas contacts the particulate material to remove at least a portion of incrementally deposited coke material on the catalyst material thereby forming a rejuvenated catalyst material and volatile hydrocarbon.

10. The process of claim 1, wherein the reheating gas enters the at least first reaction zone at a temperature of at least about 600° C. and a pressure of about 100 psia.

11. The process of claim 9, wherein at least about 10.0 wt % of the incrementally deposited coke material is removed from the catalyst material.

12. The process of claim 1, wherein the reaction interval and/or the reheating interval has a duration of about 1 min to about 90 min.

13. The process of claim 1 further comprising a regeneration interval comprising:
cyclically halting the feedstock to the first reaction zone;
supplying a regeneration gas to the first reaction zone; and
contacting the particulate material with the regeneration gas under regenerating conditions to remove at least a portion of coke material deposited on the catalyst material thereby forming a regenerated catalyst material.

14. The process of claim 13, wherein the regeneration interval occurs at an interval of every about 1 day to about 50 days.

15. The process of claim 1, wherein the first reaction zone comprises at least one heating device.

16. The process of claim 1, wherein the reaction conditions comprise a temperature of about 400° C. to about 700° C. and an outlet pressure of about 3 psia to about 30 psia.

17. The process of claim 1, wherein the particulate material further comprises an inert material.

18. The process of claim 1, wherein the catalyst material has an average diameter of about 1.0 mm to about 20.0 mm and the inert material has an average diameter of about 3.0 mm to about 20.0 mm.

19. The process of claim 17, wherein the particulate material comprises at least about 25.0 wt % inert material.

20. The process of claim 1, wherein the catalyst material comprises platinum on ZSM-5; platinum on zeolite L, and/or platinum on silica.

21. The process of claim 1, wherein the particulate material provides at least a portion (such as about 50%) of heat required for converting at least a portion of the acyclic $C_5$ hydrocarbons to the first effluent comprising cyclopentadiene.

22. The process of claim 1, further comprising a second reaction zone, and a third reaction zone operated in parallel with the first reaction zone;
wherein during the reaction interval in the first reaction zone:
a reheating interval is performed in the second reaction zone, wherein a second feedstock comprising acyclic $C_5$ hydrocarbons fed to the second reaction zone is cyclically halted; a second reheating gas is supplied to the second reaction zone and contacts a particulate material comprising a catalyst material to reheat the particulate material, and/or remove at least a portion of incrementally deposited coke material on the catalyst material thereby forming a reheated and/or rejuvenated catalyst material and a volatile hydrocarbon; and
a regeneration interval is performed in the third reaction zone, wherein a third feedstock comprising acyclic $C_5$ hydrocarbons fed to the third reaction zone is cyclically halted; a regeneration gas is supplied to the third reaction zone and contacts a particulate material comprising a catalyst material under regenerating conditions to remove at least a portion of coke material deposited on the catalyst material thereby forming a regenerated catalyst material.

23. The process of claim 1, wherein the reheating gas is substantially free of reactive oxygen-containing compounds.

24. The process of claim 1, wherein the catalyst composition is formed into a structured catalyst shape.

* * * * *